United States Patent [19]
Denis et al.

[11] Patent Number: 5,723,300
[45] Date of Patent: Mar. 3, 1998

[54] NUCLEAR LOCALIZED TRANSCRIPTION FACTOR KINASE AND DIAGNOSTIC ASSAYS RELATED THERETO

[75] Inventors: Gerald V. Denis, Arlington; Michael R. Green, Boylston, both of Mass.

[73] Assignee: University of Massachusetts Medical Center, Worcester, Mass.

[21] Appl. No.: 503,062

[22] Filed: Jul. 10, 1995

Related U.S. Application Data

[63] Continuation-in-part of Ser. No. 6,243, Jul. 19, 1993, abandoned.

[51] Int. Cl.$^6$ .................... G01N 33/53; G01N 33/573; C12Q 1/00
[52] U.S. Cl. .................... 435/7.1; 435/4; 435/7.4
[58] Field of Search .................... 435/4, 7.1, 7.4; 436/86

[56] References Cited

FOREIGN PATENT DOCUMENTS

| | | |
|---|---|---|
| WO 88/05083 | 7/1988 | WIPO . |
| WO 89/07614 | 8/1989 | WIPO . |
| WO 92/08740 | 5/1992 | WIPO . |

OTHER PUBLICATIONS

Ferrell, J. Biological Chemistry 264(34):20723–20729, 1989.
Adams et al., Nature 349:694–697, 1991.
Ahn et al., J. Biol. Chem. 265:11487–11494, 1990.
Ahn et al., J. Biol. Chem. 265:11495–11501, 1990.
Baeuerle et al., Cell 53:211–217, 1988.
Baeuerle et al., Science 242:540–546, 1988.
Banerjee et al., Proc. Nat'l Acad. Sci. USA 87:8550–8554.
Beck et al., DNA Seq. 2:203–210, 1992.
Blenis J., Cancer Cells 3:445–449, 1991.
Bohmann D., Cancer Cells 2:337–344, 1990.
Chen et al., Mol. Cell. Biol. 12:915–927, 1992.
Chung et al., Proc. Nat'l Acad. Sci. USA 88:4981–4985, 1991.
Czech et al., J. Biol. Chem. 263:11017–11020, 1988.
Devoto et al., Cell 68:167–176, 1992.
Digan et al., Dev. Biol. 114:161–169, 1986.
Dikstein et al., Cell 69:751–757, 1992.
Djabali et al., Nature Genet. 2:113–118, 1992.
Feaver et al., Cell 67:1223–1230, 1991.
Forquignon F., Wilhelm Roux's Arch. Dev. Biol. 190:132–138, 1981.
Gans et al., Genetics 96:887–902, 1980.
Gu et al., Cell 71:701–708, 1992.
Hanks S.K., Current Opinion in Structural Biology 1:369–383, 1991.
Hanks, S.K., Science 241:42–52, 1988.
Hao et al., Mol. Cell. Biol. 11:1180–1183, 1991.
Haynes et al., Dev. Biol. 134:246–257, 1989.
Hunter et al., Cell 70:375–387, 1992.
Jackson S.P., Trends Cell Biol. 2:104–108, 1992.
Jackson et al., Cell 63:155–165, 1990.
Kemp et al., Trends Biochem. Sci. 15:342–346, 1990.
Kipreos et al., Science 256:382–385, 1992.
Kozma et al., Proc. Nat'l. Acad. Sci. USA 87:7365–7369.
Leach K.L., J. Cell. Biol. 109:685–695,1989.
Lu et al., Nature 358:641–645, 1992.
Maru et al., Cell 67:459–468, 1991.
Mazo et al., Proc. Nat'l. Acad. Sci. USA 87:2112–2116, 1990.
Mitchell et al., Biochem. J. 261:131–136, 1989.
Moller et al., FEBS Lett. 186:1–7, 1985.
Nigg et al., EMBO J. 4:2801–2806, 1985.
Pelech et al., Biochem. Cell. Biol. 68:1297–1330, 1990.
Pelech et al., EDS. Plenum, New York, pp. 27–46, 1987.
Schaap et al., Eur. J. Biochem. 191:431–435, 1990.
Tkachuk et al., Cell 71:691–700, 1992.
VanEtten et al., Cell 58:669–678, 1989.
Watson et al., Proc. Nat'l. Acad. Sci. USA 79:4078–4082, 1982.
Wu et al., Cell 63:687–695, 1990.
Yu et al., J. Biol. Chem. 262:16677–16685, 1987.
Vik et al., PNAS USA 87:2685–2689.
Price et al., Science 257:973–977.
Narumiya et al., "Activation of interleukin–2 receptor gene by forskolin and cyclic amp analogues", Biochem. and Biophys. Res. Comm. 143(2):753–760, 1987.
Denis et al., "A novel, mitogen–activated nuclear kinase is related to a drosophila developmental regulator" Genes Development 10:261–271, 1995.

*Primary Examiner*—George C. Elliott
*Assistant Examiner*—Robert Schwartzman
*Attorney, Agent, or Firm*—Fish & Richardson P.C.

[57] ABSTRACT

New nuclear kinases that are regulated by signal transduction and that participate in phosphorylation cascades which regulate transcription and related methods for regulating transcription. The novel nuclear kinases play a vital role in gene expression, particularly with regard to leukemia in humans. The kinase is (i) substantially exclusively intranuclearly localized; (ii) capable of autophosphorylation; (iii) selectively bindable with antibodies raised against the RING3 portion of GST-RING3; (iv) of a molecular weight of from about 82.5 to about 92.7 kilodaltons; and (v) includes peptide sequences Asp-Ser-Asn Pro-Asp-Glu-Ile-Glu-Ile-Asp-Phe-Glu-Thr-Leu-Lys-Pro-Thr-Thr-Leu (SEQ ID NO: 1) and Ala-Val-His-Glu-Gln-Leu-Ala-Ala-Leu-Ser-Gln-Ala-Pro (SEQ ID NO: 2). The invention features a method of detecting leukemic cells in a biological sample, the method includes measuring the activity of a RING3-related kinase in the sample, an increase in the activity relative to a control being indicative of the presence of leukemic cells.

10 Claims, 7 Drawing Sheets

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: Not Relevant ( D ) TOPOLOGY: linear ( i i ) MOLECULE TYPE: protein ( x i ) SEQUENCE DESCRIPTION: SEQ ID NO:1:

Asp Ser Asn Pro Asp Glu Ile Glu Ile Asp Phe Glu Thr Leu Lys Pro
1               5                   10                  15

Thr Thr Leu ( 2 ) INFORMATION FOR SEQ ID NO:2:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:2:

Ala Val His Glu Gln Leu Ala Ala Leu Ser Gln Ala Pro
1               5                   10

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:3:

Lys Lys Lys Arg Lys
1               5

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:4:

Gly Xaa Xaa Xaa Xaa Gly Lys
1               5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:5:

Gly Xaa Gly Xaa Xaa Gly
1               5

( 2 ) INFORMATION FOR SEQ ID NO:6:

( i ) SEQUENCE CHARACTERISTICS:
        ( A ) LENGTH: 21 amino acids ( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:6:

```
Gly Ala Gly Ser Val Gly Gly Val Gly Gly Ala Gly Ala Ala Gly Gly
 1               5                   10                  15
Gly Asn Ala Ser Lys
                20
```

( 2 ) INFORMATION FOR SEQ ID NO:7:

( i ) SEQUENCE CHARACTERISTICS:
( A ) LENGTH: 21 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:7:

```
Gly Ala Gly Gly Phe Gly Ser Val Tyr Lys Ala Thr Tyr Arg Gly Val
 1               5                   10                  15
Pro Val Ala Ile Lys
                20
```

( 2 ) INFORMATION FOR SEQ ID NO:8:

( i ) SEQUENCE CHARACTERISTICS:
( A ) LENGTH: 11 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:8:

```
Tyr His Asp Ile Ile Lys Xaa Pro Xaa Xaa Leu
 1               5                   10
```

( 2 ) INFORMATION FOR SEQ ID NO:9:

( i ) SEQUENCE CHARACTERISTICS:
( A ) LENGTH: 4 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:9:

```
Ala Pro Glu Phe
 1
```

( 2 ) INFORMATION FOR SEQ ID NO:10:

( i ) SEQUENCE CHARACTERISTICS:
( A ) LENGTH: 4 amino acids
( B ) TYPE: amino acid
( C ) STRANDEDNESS: Not Relevant
( D ) TOPOLOGY: linear ( i i ) MOLECULE TYPE: protein ( x i ) SEQUENCE DESCRIPTION: SEQ ID NO:10:

```
Ala Gln Glu Phe
 1
```

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:11:

```
Asp Val Val Ala Met Xaa Arg Lys Leu
1               5
```

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:12:

```
Tyr Ala Lys Met
1
```

( 2 ) INFORMATION FOR SEQ ID NO:13:

( i ) SEQUENCE CHARACTERISTICS:
        ( A ) LENGTH: 19 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:13:

```
His Arg Leu Ala Glu Xaa Xaa Xaa Xaa Xaa Xaa Xaa Xaa His Glu Gln
1               5                   10                  15
Leu Ala Ala
```

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:14:

```
Arg Arg Leu Ser Ser Arg Ala
1               5
```

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:15:

```
Ala Pro Arg Thr Pro Gly Gly Arg Arg
1               5
```

( 2 ) INFORMATION FOR SEQ ID NO:16:

( i ) SEQUENCE CHARACTERISTICS:
      ( A ) LENGTH: 10 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:16:

```
Arg Arg Arg Glu Glu Glu Thr Glu Glu Glu
1               5                   10
```

( 2 ) INFORMATION FOR SEQ ID NO:17:

( i ) SEQUENCE CHARACTERISTICS:
      ( A ) LENGTH: 13 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:17:

```
Arg Phe Ala Arg Lys Gly Ser Leu Arg Gln Lys Asn Val
1               5                   10
```

( 2 ) INFORMATION FOR SEQ ID NO:18:

( i ) SEQUENCE CHARACTERISTICS:
      ( A ) LENGTH: 10 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:18:

```
Pro Leu Ser Arg Thr Leu Ser Val Ser Ser
1               5                   10
```

( 2 ) INFORMATION FOR SEQ ID NO:19:

( i ) SEQUENCE CHARACTERISTICS:
      ( A ) LENGTH: 13 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:19:

```
Leu Leu Arg Pro Gln Arg Ala Thr Ser Asn Val Phe Ser
1               5                   10
```

( 2 ) INFORMATION FOR SEQ ID NO:20:

( i ) SEQUENCE CHARACTERISTICS:
      ( A ) LENGTH: 7 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:20:

```
Leu Arg Arg Ala Ser Leu Gly
1               5
```

( 2 ) INFORMATION FOR SEQ ID NO:21:

( i ) SEQUENCE CHARACTERISTICS:
        ( A ) LENGTH: 19 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:21:

```
Asp Ser Asn Pro Asp Glu Ile Glu Ile Asp Phe Glu Thr Leu Lys Pro
1               5                   10                  15
Thr Thr Leu
```

( 2 ) INFORMATION FOR SEQ ID NO:22:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:22:

```
Ala Val His Glu Gln Leu Ala Ala Leu Ser Gln Ala Pro
1               5                   10
```

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:23:

```
Gly Xaa Gly Xaa Xaa Gly
1               5
```

( 2 ) INFORMATION FOR SEQ ID NO:24:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
CGCCGCGGAT CCATGGCTTC GGTGCCTGCT                              30
```

( 2 ) INFORMATION FOR SEQ ID NO:25:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
GGCTGGGAAT TCAATGTT                                           18
```

NUCLEAR LOCALIZED TRANSCRIPTION FACTOR KINASE AND DIAGNOSTIC ASSAYS RELATED THERETO

CROSS REFERENCE TO RELATED APPLICATIONS

This application is a continuation-in-part of U.S. Ser. No. 08/006,243, filed Jan. 19, 1993, now abandoned.

STATEMENT AS TO FEDERALLY SPONSORED RESEARCH

The studies described herein were supported, in part, by NIH grant AI 07272-09. The United States government may have some rights in the invention.

BACKGROUND OF THE INVENTION

The study of how the phosphorylation of proteins by protein kinases regulates eukaryotic transcription has enjoyed rapid progress. It has long been known that many extracellular receptors transfer structural information from hormones and growth factors into phosphorylation information. A well understood and growing set of cytosolic kinases, including protein kinase A, protein kinase C, calcium calmodulin-dependent kinases, oncogene-encoded kinases, casein kinase II, glycogen synthase kinase III and the erk-encoded family of kinases, have been shown to contain biochemical signals destined for the nucleus (Czech et al., 1988; Bohmann, 1990; Blenis, 1991; Jackson, 1992). In the nucleus, phosphorylation has been shown to affect both the DNA-binding activity and the transcriptional activation of several transcription factors, some positively and some negatively (Hunter and Karin, 1992). Activated transcription of "immediate early genes" seems to be conducted primarily through phosphorylation.

However, efforts to date to delineate pathways of information flow from receptor to promoter have tended to focus on the physical extension of cytosolic signalling cascades into the nucleus, for example, by demonstrations of nucleus-cytosol partitioning of transcription factor substrates and nuclear forms of cytosolic kinases (Hunter and Karin, 1992). Cytosolic protein kinase C has been shown to phosphorylate the NFkB-IkB complex in the cytosol, leading to dissociation of the complex, whereupon transcriptionally active NFkB partitions into the nucleus (Baeuerle and Baltimore, 1988a; b). Furthermore, a number of kinases that are activated by extracellular signals appear to translocate to the nuclear membrane (or to a nuclear fraction) upon mitogenic stimulation of the cell, notably protein kinase A (Nigg et al., 1985; Adams et al., 1991), protein kinase C (Leach et al., 1989), microtubule-associated protein/myelin basic protein (MAP/MBP) kinase and ribosomal S6 kinase (RSK) (Chen et al., 1992). Some kinases that phosphorylate nuclear targets seem to be activated in the cytosol, such as the cellular homolog of c-abl (Van Etten et al., 1989; Dikstein et al., 1992; Kipreos and Wang, 1992); whereas the partitioning behavior of others is either not known to be regulated, such as FER (Hao et al., 1991) and Sp1 kinase (Jackson et al., 1990); or is poorly understood, such as the transcription complex-associated kinase that phosphorylates the C-terminal domain of RNA polymerase II (Feaver et al., 1991; Lue et al., 1992) and p33$^{cdk2}$, which is present in a complex with the transcription factor E2F, cyclin A and p107 (Devoto et al., 1992).

While these physical translocations are undoubtedly important features of signal transduction, they provide no suggestion that there might also exist signalling kinases that are downstream targets of cytosolic kinases but that are restricted solely to the nucleus.

SUMMARY OF THE INVENTION

Nuclear kinases that are regulated by signal transduction and that participate in phosphorylation cascades which regulate transcription and related methods for regulating transcription and detecting disease states are described. The novel nuclear kinases play a vital role in gene expression, particularly with regard to the expression of genes involved in leukemia in humans.

Described herein is a novel kinase characterized as follows: (i) substantially exclusively intranuclearly localized; (ii) capable of autophosphorylation; (iii) selectively bindable with antibodies raised against the RING3 portion of GST-RING3; (iv) of a molecular weight of from about 82.5 to about 92.7 kilodaltons; and (v) includes peptide sequences Asp-Ser-Asn-Pro-Asp-Glu-Ile-Glu-Ile-Asp-Phe-Glu-Thr-Leu-Lys-Pro-Thr-Thr-Leu (SEQ ID NO: 1) and Ala-Val-His-Glu-Gln-Leu-Ala-Ala-Leu-Ser-Gln-Ala-Pro (SEQ ID NO: 2). This kinase is referred to herein as the "90 kD kinase." The 90 kD kinase has the additional characteristic of being able to phosphorylate a myelin basic protein substrate in vitro. The 90 kD kinase is closely related to human RING3 (herein RING3) described in Beck et al. (1991). The 90 kD kinase may actually be the protein identified as human RING3. In any event, the 90 kD kinase is an example of a "RING3-related kinase." By "RING3-related kinase" is meant the 90 kD kinase described herein, RING3, and Genbank Accession D26362. These proteins are members of a family of proteins (which may have other members) that can autophosphorylate, phosphorylate myelin basic protein in vitro, are part of a signalling pathway, and are highly homologous (at the protein sequence level) to human RING3. Included in the family are allelic variants of the 90 kD kinase, human RING3, and the protein identified by Genbank Accession D26362.

The invention features a biochemical assay for the presence of leukemic cells. The assay entails measuring the activity of the above-described 90 kD kinase (or RING3) in a biological sample comprising hematopoietic cells (e.g., a blood sample, a bone marrow sample, or a spleen sample). The assay can be used to diagnose acute lymphocytic leukemia, chronic lymphocytic leukemia, acute myelogenous leukemia, and other forms of leukemia. By "leukemic cells" is meant abnormal hematopoietic cells generally having the following characteristics: (1) poor responsiveness to normal regulatory mechanisms; (2) diminished capacity for normal differentiation; (3) ability to expand at the expense of normal lymphoid or myeloid cell lines; and (4) ability to suppress or interfere with the growth of normal lymphoid or myeloid cells. Leukemic cells are cells which overproliferate relative to normal hematopoietic cells. The method of the invention can be used to detect the presence of myeloid or lymphoid leukemias. In addition to detecting leukemic cells, the method of the invention may be used to provide a measure of the agressiveness of leukemic cell overproliferation. Thus, both the relative number of leukemic cells and their potential for rapid proliferation may be estimated.

The level of 90 kD kinase activity can be used to judge the stage of a patient's leukemic condition. It may be used for the initial diagnosis of leukemia or to determine whether (or if) a patient already diagnosed with leukemia, but in remission, is at risk for relapse.

There are a wide range of assays which can be used measure 90 kD kinase activity. The autophosphorylation activity of the 90 kD kinase is correlated with its activation. Thus, one can measure activated 90 kD kinase by measuring the level of autophosphorylation. This can be done by allowing autophosphorylation to occur in the presence [γ-$^{32}$P]ATP or some other detectable label. Activity of the 90 kD kinase can also be determined by measuring the its ability to phosphorylate a substrate such as myosin light chain kinase peptide, Kemptide, or myelin basic protein.

Alternatively, an antibody specific for the phosphorylated form of 90 kD kinase can be used to measure 90 kD kinase activity by measuring the level of phosphorylated 90 kD kinase (or RING3-related kinase) using an ELISA assay or other antibody based protein detection and quantification assays.

The 90 kD kinase has some homology to fsh (Drosophila) and RING3 (human). Human RING3 was found to possess protein kinase activity. RING3 is attributed with a role consistent with that of the novel kinase. In some cases assays used to detect RING3 or RING3 activity can be used to detect 90 kD kinase or 90 kD kinase activity.

Thus, the invention features a method of detecting leukemic cells in a biological sample. The method includes measuring the activity of a RING3-related kinase in the sample, an increase in the activity relative to that present in a control being indicative of the presence of leukemic cells.

Suitable controls include similar biological samples known to contain little or no active 90 kD kinase, e.g., a biological sample from a patient known not to be suffering from leukemia (or other cancers). Preferably the biological sample is of the same type as the test sample (e.g., both are whole blood samples). Other suitable controls are non-biological standards known not to contain significant levels of active 90 kD kinase. Test kits which include such a negative control sample and/or a positive control sample (a sample known to contain active 90 kD kinase (or RING3) are an aspect of the present invention.

In various preferred embodiments the biological sample comprises lymphocytes, the activity is measured by assaying the autophosphorylation activity of a RING3-related kinase, the activity is measured by assaying phosphorylation of a substrate of a RING3-related kinase, the activity is measured by measuring autophosphorylation activity, and autophosphorylation activity is measured by immunological methods.

In another preferred embodiment, the RING3-related kinase activity is measured in a first and a second biological sample, a higher level of RING3-related kinase activity in the first biological sample relative to the second biological sample indicating the presence of more leukemic cells in the first biological sample than in the second biological sample. In even more preferred embodiments the first and second biological samples are obtained from the same patient at different times, and the second biological sample is obtained from an individual that is not suffering from a leukemic condition.

In another aspect, the invention features a kit for detecting leukemic cells in a biological sample, the kit includes a substantially pure antibody that specifically recognizes an autophosphorylated form of a RING3-related kinase.

Other features and advantages of the invention will be apparent from the following detailed description thereof, and from the claims.

DETAILED DESCRIPTION

Figure 1A:
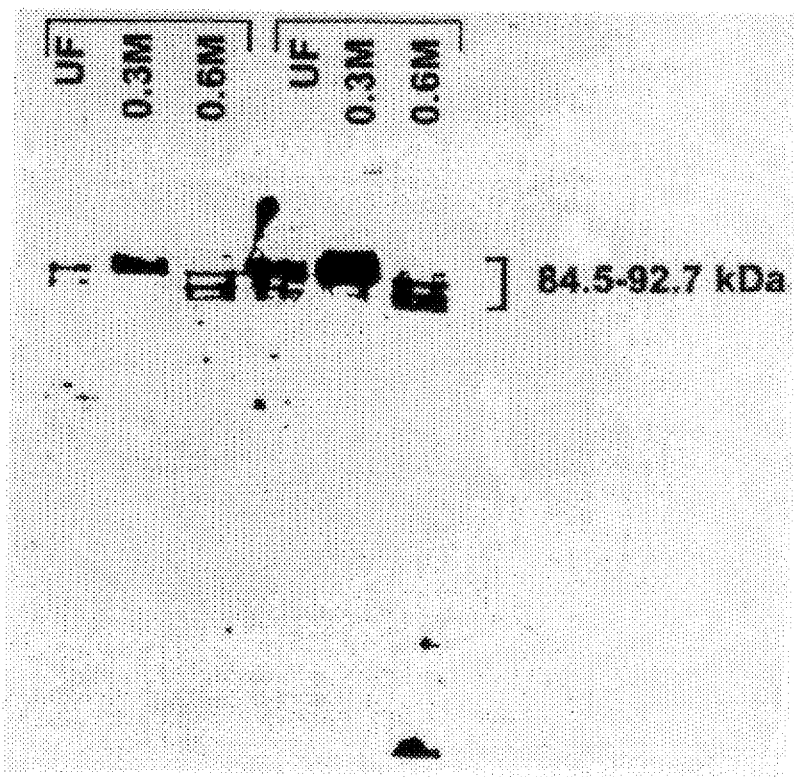
FIG. 1A: Autophosphorylation of a 90 kD kinase in Jurkat cells is increased by forskolin treatment. Nuclear extracts from forskolin-treated and control Jurkat cells were fractionated on phosphocellulose columns. The columns were eluted stepwise with 0.3M and 0.6M sodium chloride in buffer. Eluted proteins were precipitated with trichloroacetic acid, solubilized in sodium dodecyl sulfate, separated by gel electrophoresis, electroblotted to nitrocellulose, denatured in guanidine hydrochloride, renatured in buffer, and assayed by autophosphorylation in the presence of [γ-$^{32}$P]ATP and magnesium. Autoradiographs of blots are shown. Unfractionated nuclear extracts (UF) are included for comparison.

Regulated transcription of eukaryotic nuclear genes depends in part on the accurate processing of information about the extracellular milieu, especially hormone, growth factor, drug, or other ligand binding to plasma membrane (cell surface) receptors. This information is processed through multiple kinase cascades within the cell, ultimately giving rise to the activation of transcription factors in the nucleus. It is of vital interest to identify the kinases that play a role in this transduction of signals and to delineate the signalling networks involved.

In accordance with the invention it was reasoned that there must be many uncharacterized kinases that are mostly or entirely localized to the nucleus, that receive signals transduced from the cytosol and then go on to phosphorylate and activate nuclear components of the transcription apparatus.

In the process of arriving at the invention, nuclear extracts of cultured cell lines were screened for previously uninvestigated kinases that exhibit regulated activity and that might phosphorylate transcription factors. In order to increase the likelihood that such a kinase is important in transcription, its principal features were considered to include primarily (although not necessarily exclusively) nuclear localization, and responsiveness to drugs, hormones or conditions that are known independently to promote transcription in cultured cells.

A straightforward screen of nuclear extracts of Jurkat cells, performed by adding magnesium and [γ-$^{32}$P]ATP to the extract, incubating it, and identifying the proteins by denaturing gel electrophoresis and autoradiography, did not reveal any obvious differences in phosphorylation between the proteins from cells stimulated with phorbol myristate acetate/phytohemagglutinin and controls. Too many phosphorylated proteins obscured potential differences.

In accordance with the invention, this problem was addressed and overcome by nitrocellulose electroblotting gels of electrophoretically separated proteins, denaturing the blotted proteins in guanidine hydrochloride (e.g., 7M), renaturing them in buffer and then probing the blot with [γ-$^{32}$P] ATP (Ferrell and Martin, 1989). This assay visualized only those kinases which could renature after gel electrophoresis in sodium dodecyl sulfate and could autophosphorylate.

A previously uncharacterized autophosphorylation activity has now been identified in HeLa nuclear extract. Denaturing polyacrylamide gels of nuclear proteins were electroblotted to nitrocellulose, renatured and assayed for autophosphorylated bands by overlaying the blots with [γ-$^{32}$P]ATP and magnesium ion. Autoradiography of the blots visualized a limited set of kinases, one of which was predominantly nuclear and which exhibited rapidly increased autophosphorylation in forskolin-stimulated Jurkat cells and both serum and forskolin-stimulated A431 cells.

A forskolin analog with greater water solubility and activity approximately equal for forskolin was used in these studies. This analog is called 7β-deacetyl-7β(γ-N-methylpiperazino)-butyryl forskolin and is supplied by Calbiochem as product number 344273. Because forskolin is a potent activator of adenylate cyclase, other pharmacological agonists of adenylate cyclase, such as other derivatives of forskolin, are expected to stimulate the activity of the 90 kD kinase in a similar manner. By the same token, other drugs, hormones or growth factors that increase the intracellular activity of cyclic AMP-dependent protein kinase, which is the target of the cyclic AMP produced by adenylate cyclase, are also expected to stimulate the 90 kD kinase. These other drugs or hormones include membrane-permeable derivatives of cyclic AMP, such as its dibutyryl ester or "caged" cyclic AMP; isoproterenol, glucagon, epinephrine, bombesin or other agents that mobilize cyclic AMP in their responsive cell types; and other as yet uncharacterized factors in serum that mobilize cyclic AMP. In addition, agents that inhibit phosphodiesterase, which destroys the cyclic AMP, will increase intracellular cyclic AMP concentrations and by mobilizing cyclic AMP-dependent protein kinase, are expected to increase the activity of the 90 kD kinase. Phosphodiesterase inhibitors include such agents as 3-isobutyl-1-methylxanthine. Finally, DNA expression vectors that encode the catalytic subunit of protein kinase A will also increase the intracellular activity of protein kinase A and are thereby expected to increase the activity of the 90 kD kinase.

The kinase activity resolved as a multiplet of average apparent molecular mass 90 kD on SDS gels. Phosphocellulose chromatography fractionated the multiplet into forms of slightly slower and faster mobility. The forms of slightly slower mobility on SDS gels bound more weakly to phosphocellulose than the forms of slightly faster mobility, probably due to hyperphosphorylation, and these exhibited both increased autophosphorylation and increased substrate-directed phosphorylation if they were isolated from cells that had been stimulated with serum or forskolin. Analogous phenomena have been observed with pp70$^{s6K}$ (Price et al., 1992) and pp90$^{rsk}$ (Vik et al., 1990) S6 kinases, for which the higher phosphorylated forms exhibit both reduced mobility on SDS gels and increased substrate-directed phosphorylation. This pattern, in which increased phosphorylation of the kinase reflects increased substrate-directed activity, is observed also with protein kinase C (Mitchell, et al., 1989) and appears to define a subclass of intracellular signalling kinases.

This 90 kD autophosphorylation activity appears to be ubiquitous, as it was observed in every mammalian cell line assayed. Its presence in yeast, Drosophila or plants has not yet been determined. The occurrence of well-resolved autophosphorylating kinases of the same apparent mobility in a wide variety of cells was consistent with the fact that the renaturation assay that was used selected for independently refolding catalytic domains that do not require protein disulfide isomerase or chaperonin activity to regain function. Such stably folded kinases are likely to share certain structural features of folding pathways that are conserved in different organisms.

Autophosphorylation was dramatically reduced to a basal level when the extracts were prepared in the absence of phosphatase inhibitors or when extracts were warmed to 37° C. in the presence of 5 mM magnesium ion, thereby eliminating differences between extracts prepared from control or stimulated cells, a frequently observed feature of signal-transducing kinases (Kozma et al., 1990). Without being bound by any particular theory, these observations point to the interpretation that the 90 kD kinase is probably rapidly and reversibly phosphorylated and activated by an intracellular signal transduction pathway. These changes to autophosphorylation activity were remarkably stable, a phenomenon that has been observed among certain kinases involved in signal transduction, such as RSK and MAP kinases (Ahn et al., 1990).

Consistent with a large body of work on "switch kinases" and nuclear phosphorylation (Ahn and Krebs, 1990; Pelech et al., 1987; 1990) that has failed to detect phosphotyrosine phosphorylation in the nucleus, the 90 kD species contained no phosphotyrosine, and phosphorylated its myelin basic protein substrate only on serine. Myelin basic protein is used frequently as an in vitro substrate for MAP kinases, and its suitability here suggested that the 90 kD kinase might share some structural or functional similarities with the members of the MAP kinase family or with the RSK family, which is immunologically related to the MAP kinases. However, the 90 kD kinase did not phosphorylate a range of substrates, including peptide substrates for S6 kinase, MAP kinase, casein kinase II, glycogen synthase kinase III, protein kinase C, calcium-calmodulin-dependent protein kinase, or Raytide (a general substrate for tyrosine kinases). It did phosphorylate peptide substrates for smooth muscle myosin light chain kinase and for protein kinase A and was active in the absence of cofactors. These substrate peptides have at least two hydrophobic, basic amino acids that are positioned two residues toward the N-terminus from a phosphorylatable serine (Kemp and Pearson, 1990). Amino acid sequence analysis of the phosphorylation site and site-directed mutagenesis will provide more information about the substrate requirements of the kinase. The nuclear localization of the enzyme and its lack of immunoreactivity with rabbit polyclonal antibodies to protein kinase C, RSK or MAP kinases indicated that the 90 kD kinase was unlike other previously characterized kinases.

This question of its identity was most effectively resolved by purification and microsequencing of the protein. The initial strategic choice to look for activities that were renaturable on nitrocellulose after electrophoresis in SDS and electroblotting proved to have an added benefit of disqualifying those kinases that rapidly lose activity during purification. The great stability of the activity made purification easier. THis characteristic of the 90 kD kinase can be exploited to rapidly carry out partial purifications where required to accurately measure the level of activated 90 kD kinase. Classical protein purification techniques yielded activity in sufficient purity and quantity to obtain a microsequence of two internal peptides. One of these peptides produced a significant match with both the Drosophila fsh gene (DROFSHB) (Haynes et al., 1989) and with the human RING3 gene (HUMRING3) (Beck et al., 1991), whereas the other matched only RING3. This result implied that these genes encoded functional kinases, which has not been reported in the literature. Bacterially expressed cDNAs for these genes failed to exhibit autophosphorylation in vitro unless they were incubated with HeLa nuclear extract. Rabbit polyclonal antibodies raised against two bacterially expressed N-terminal fusions of the human and Drosophila cDNAs with glutathione-S-transferase were capable of immunoprecipitating the original 90 kD autophosphorylation activity from HeLa nuclear extract, whereas preimmune sera were not. Open reading frames for fsh identify gene products of molecular weight 110,000 and 205,000 for 5.9 kb and 7.6 kb mRNA transcripts, respectively (Haynes, et al., 1989), which is at variance with the apparent molecular mass of the activity isolated from HeLa nuclear extract. Post-translational proteolytic cleavage of the fsh gene products to give active kinase may account for this discrepancy; such proteolytic activation of kinases is well exemplified by protein kinase C cleavage to yield constitutively active protein kinase M (Schaap, et al., 1990). The open reading frame for RING3, on the other hand, identifies a gene product of molecular weight 83,000 (Beck et al., 1991) which could account for the apparent molecular masses observed, especially for a phosphorylated gene product (Kozma et al., 1990).

Consistent with the apparently nuclear localization of the HeLa 90 kD kinase, the RING3 gene possesses a putative nuclear localization sequence (KKKRK (SEQ ID NO: 3), at amino acid 508; Beck et al., 1991); however, this sequence is absent from fsh and lies upstream from a C-terminal domain of homology (170 amino acids, 72% identity) that the two genes share (Beck et al., 1991). This region of homology contains some elements of a putative kinase catalytic domain.

Subdomain Structure

The molecular organization of fsh and RING3 is somewhat unusual. A putative phosphate binding motif GXXXXGK (SEQ ID NO: 4) (Moller and Amons, 1985) is located at amino acid residue 809 in fsh, and a putative ATP-binding motif GXGXXG (SEQ ID NO: 5) (Hanks et al., 1988) is found at amino acid position 880 in fsh and 557 in RING3. Fifteen residues downstream from the last glycine of GXGXXG (SEQ ID NO: 5) in fsh and 11 downstream in RING3 lies a putative catalytic lysine residue, which is in both cases two residues downstream from an alanine that is conserved in many kinases. This sequence in fsh (GAG SVG GVG GAG AAG GGN ASK (SEQ ID NO: 6)), is most highly related to the corresponding subdomains of c-mos (GAG GFG SVY KAT YRG VPV AIK (SEQ ID NO: 7); Watson et al., 1982). A run of glutamates 43 residues downstream from the putative catalytic lysine in fsh and 13 downstream in RING3 identifies a putative subdomain III within a C-terminal region of significant sequence homology between fsh and RING3. Another motif, DFE, at position 997 in fsh and 640 in RING3, suggests subdomain VII (DFG). An interesting extended run of serines at the C-terminus of the open reading frame may function as an autophosphorylation or autoinhibitory domain (Banerjee et al., 1990). Despite these sequence similarities, some of the conserved subdomains that ordinarily occur downstream from the putative DFG motif are missing in fsh and RING3 because the open reading frame ends.

However, lack of certain consensus motifs does not mean that a particular open reading frame cannot encode a kinase (Wu et al., 1990; Maru and Witte, 1991). Strangely, in fact, putative subdomains occur in an appropriate order in the middle of the open reading frame of each gene, in a different region of significant homology between fsh and RING3. Here, a motif YHDIIKXPXXL (SEQ ID NO: 8) suggests subdomain VIB; a motif APEF (SEQ ID NO: 9) in fsh and AQEF (SEQ ID NO: 10) in RING3 suggests subdomain VIII; a motif DVVAMXRKL (SEQ ID NO: 11) suggests domain IX; a motif YAKM (SEQ ID NO: 12) in RING3 suggests subdomain X and HRLAEXXXXXXXXHEQLAA (SEQ ID NO: 13) in RING3 suggests subdomain XI. This unusual overall structure is not incompatible with kinase catalytic activity and may have arisen through exon shuffling. Another signal-transducing kinase, S6 kinase II from chicken and Xenopus, possesses two catalytic domains that are homologous to protein kinase C and substrate recognition domains homologous to phosphorylase kinase. This structure has also been proposed to arise from exon shuffling (Banerjee et al., 1990). We have been unable to identify other kinases in the GenBank database that exhibit similar organization or that have regions of homology with fsh and RING3 that extend much beyond the individual subdomains discussed here.

Most intriguing is the potential role that these genes may play in development and transformation. In Drosophila, mutations in the fsh locus exhibit a homeotic phenotype. The gene is required at two stages in development: once during early embryogenesis, where there arises a maternal effect that cannot be rescued by sperm carrying the wild type allele (Forquignon, 1981), and again during pupation, where the effect is zygotic and the numbers of progeny with the mutant phenotype decreases with increasing dose of the wild type allele (Gans et al., 1980). These two periods are temperature-sensitive and at the restrictive temperature, the effect is lethal. At semipermissive temperatures, heterozygous progeny can reach adulthood, but have a high frequency of organ deficiencies and transformations of the third thoracic segment to the second thoracic segment. This phenotype resembles transformations in the bithorax complex of genes, and indeed, mutations in certain bithorax genes such as trithorax (also called Regulator-of-bithorax) and Ultrabithorax[130] are closely linked to fsh and show increased severity with hypodosage of wild type fsh (Forquignon, 1981). Trithorax (Genbank accession number M31617), which is required during embryogenesis and later, requires activation by fsh (Digan et al., 1986) and has a number of putative zinc fingers that indicate it is likely to be a transcription factor (Mazo et al., 1990). In light of this evidence, we propose that fsh is a kinase that phosphorylates trithorax, thereby activating trithorax directed transcription of developmentally important genes. The N-terminal domain of the open reading frame of trithorax has several phosphorylation motifs of the type (R/K)(R/K)XX(S/T), which can be recognized by protein kinase A and myosin light chain kinase (Kemp and Pearson, 1990). The substrate specificity of the 90 kD kinase described above is not inconsistent with an ability to phosphorylate trithorax.

The biological role of RING3 is less well understood. Its occurrence in the major histocompatibility complex among a set of recently characterized genes that do not appear to have a role in antigen processing suggests that if it is a nuclear kinase in human cells, there may be a human homolog of trithorax that has zinc fingers and that functions as its transcription factor substrate. In this regard, a recent report that maps the breakpoint in chromosomal translocations of human chromosome 11 has identified an interrupted gene with significant homology to trithorax (Djabali et al., 1992). This t(4;11)(q21;q23) reciprocal translocation is associated with acute lymphocytic leukemia in children, which may represent a biological consequence of loss-of-function of the human trithorax homolog. In addition to putative zinc fingers, the homolog has "AT hook" motifs that may be involved in binding to the minor groove of DNA (Tkachuk et al., 1992). In-frame fusions of this human homolog, called the ALL-1 gene (Gu et al., 1992) to the AF-4 gene as a result of the reciprocal translocation may give rise to a new protein with oncogenic transforming potential (Tkachuk et al., 1992; Gu et al., 1992). Alternatively, deletion of important regulatory sites of phosphorylation in ALL-1 by the translocation may account in part for the oncogenic effects. In such a case, we would predict by analogy that alteration-of-function mutations in RING3 might be associated with leukemia as well. Further characterization of the relationship between RING3 and the trithorax homolog might illuminate the genomic organization of RING3 within the major histocompatibility locus and its expression in T-cells (Beck et al., 1991) as well as the emerging parallel relationships between the important players in Drosophila development and human cancer.

EXAMPLE 1

Characterization of Transcription Factor Nuclear Kinases
Materials

Dextran sulfate (average molecular weight 500,000), insulin, glucagon, acidic fibroblast growth factor, reactive green-19 and Cibacron Blue 3GA (Type 3000) agarose were from Sigma. Sodium orthovanadate, Tris, trichloroacetic acid, $MgCl_2$ and NaOH were from Fisher. Disodium ATP and NP-40 were from Pharmacia LKB. Guanidine hydrochloride was from Fluka. Phytohemagglutinin-M, phorbol 12-myristate 13-acetate, calcium ionophore A23187, human interleukin-2, (7β-deacetyl-7β-[-N methylpiperazino]-buytyrl)-forskolin dihydrochloride and rat brain protein kinase C were from Calbiochem. Wheat germ extract and rabbit reticulocyte extract systems for in vitro translation were from Promega. Raytide and recombinant $p43^{v-abl}$ were from Oncogene science (Uniondale, N.Y.). In vitro phosphorylation substrates were from Peninsula Laboratories (Belmont, Calif.). [α- and γ-$^{32}$P]ATP were from New England Nuclear. Nitrocellulose membranes were from Micron Separations (Westboro, Mass.) and polyvinyl difluoride membranes (PVDF) were from Millipore. Recombinant protein A-agarose was from Repligen (Cambridge, Mass.). Phosphocellulose resin (P-11) was from Whatman. Polyacrylamide monomer, bisacrylamide and ammonium persulfate were from National Diagnostics (Manville, N.J.). Cell culture media, calf serum, monoclonal antibody Mab 1.9 against rat brain protein kinase C and TEMED were from GIBCO-BRL. Fetal bovine serum for Jurkat cell culture was from Whittaker Bioproducts (Walkersville, Md.). Cell lines (HeLa, ATCC CCL 2; A431, ATCC CRL 1555; Jurkat, ATCC TIB 152; HUT78, ATCC TIB 161; Mvl Leu, ATCC CCL64; CHO DUKX B1, ATCC CRL 901 0; CV-1, ATCC CCL70; and COS-7, ATCC CRL 1651) were obtained from ATCC and cultured as advised. Jurkat clone E6-1 (Weiss et al., 1984) and HUT78 (Gazdar et al., 1980) were obtained through the AIDS Research and Reference Reagent Program, Division of AIDS, NIAID, NIH. 3T3-L1 fibroblasts (ATCC CL 173) were the kind gift of Michael P. Czech, University of Massachusetts Medical Center, and were differentiated according to Rubin et al. (1978). An Epstein-Barr virus-transformed human B-cell line (32D clone 13) (FitzGerald et al., 1991) was obtained from Joel Greenberger, University of Massachusetts Medical Center. Human peripheral blood lymphocytes from normal, healthy volunteers, were the kind gift of John Sullivan University of Massachusetts Medical Center. Rabbit polyclonal antisera to purified GST fusion proteins were prepared by Berkeley Antibody Company (Richmond, Calif.). Platelet-derived growth factor was the kind gift of Roger J. Davis, University of Massachusetts Medical Center. Rabbit anti-rat MAP kinase (erk-1 C-terminal 333–367 amino acids) polyclonal antibody was from Upstate Biotechnology (Lake Placid, N.Y.) and anti-RSK rabbit antibody was the kind gift of John Blenis, Harvard Medical School. HeLa nuclear extract was prepared with 1 mM sodium vanadate and 50 mM β-glycerophosphate after the method of Dignam et al. (1983). All other reagents were from Sigma.

Renaturation assay

Proteins were separated in polyacrylamide gels according to Laemmli (1970) and electroblotted to nitrocellulose or PVDF membranes. Blotting was performed in 25 mM Tris, 192 mM glycine, 10% methanol at 100 mA for one hour at room temperature. The blots were incubated in 7M guanidine HCl, 50 mM Tris-HCl pH 8.5, 50 mM DTT and 2 mM EDTA for one hour at room temperature to denature blotted proteins, then transferred to ice-cold buffer containing 100 mM NaCl, 50 mM Tris-HCl, 2 mM DTT, 2 mM EDTA and 0.1% NP-40. Proteins were renatured overnight at 4° C. in this buffer. The blots were then blocked with 5% dextran sulfate in the same buffer for one hour at room temperature; then incubated for one hour at room temperature with 0.15 mCi/ml [γ-$^{32}$P]ATP (25 nM) in 30 mM Tris-HCl pH 8.0, 30 mM MgCl$_2$, 2 mM DTT, 0.2 mM EDTA and 0.1% NP-40; and washed sequentially for ten minutes each with: 50 mM Tris-HCl pH 8.0; 0.1% NP-40 in 50 mM Tris-HCl pH 8.0; 50 mM Tris-HCl pH 8.0; 1M NaOH; 10% acetic acid and then water, after Ferrell and Martin (1989). The blots were then autoradiographed at −80° C.

For phosphorylation of protein or peptide substrates in solution, nitrocellulose strips of immobilized, renatured kinase were excised and placed in Eppendorf tubes with 30 mM Hepes pH 8.0, 30 mM MgCl$_2$ (or 1 mM MnCl$_2$), 2 mM DTT, 0.5 mM EDTA, 0.1% NP-40, 10 μM disodium ATP, 0.15 mCi/ml [γ-$^{32}$P]ATP and 1 mg/ml myelin basic protein or 1 mg/ml peptide substrate in a final volume of 10 μl. Reactions were allowed to proceed for one hour at 30° C., whereupon protein phosphorylation reactions were quenched with SDS sample buffer and heated to 100° C. Phosphorylated protein samples were separated by SDS PAGE and visualized by Coomassie Blue staining and autoradiography. Peptide phosphorylation reactions were quenched with 4 volumes of ice-cold 10% phosphoric acid. Phosphorylated peptide samples were applied to 0.1 ml columns of phosphocellulose that had been prequilibrated with 0.5% phosphoric acid. Columns were washed extensively with 0.5% phosphoric acid and radioactivity that remained in the columns was quantified by Cerenkov counting.

Phosphoaminoacid analysis

HeLa nuclear extract was fractionated on phosphocellulose and proteins that eluted at 0.3M and 1.0M NaCl were precipitated with TCA, washed with acetone, solubilized in SDS, separated on an 8% polyacrylamide gel, electroblotted to PVDF, denatured in guanidine Hydrochloride and renatured as described. PVDF strips were excised, placed in Eppendorf tubes and incubated with [γ-$^{32}$P]ATP without unlabelled ATP as described. The autophosphorylated kinases were then hydrolyzed in 6N HCl at 110° C. for one hour, according to Lewis et al. (1990). The acidic solution was diluted five-fold with water: methanol (50:50; v:v) and lyophilized twice. The lyophilization residue was dissolved in 30% formic acid and spiked with phosphoaminoacid standards. Equal amounts of radioactivity (about 2000 cpm by Cerenkov counting) were applied to a cellulose thin layer plate. Phosphoaminoacids were separated by electrophoresis in glacial acetic acid: pyridine: water (10:1:89; v:v:v) at pH 3.5 for two hours at 1000 V and visualized with ninhydrin. Radioactive spots were visualized by autoradiography.

Protein purification

HeLa nuclear extract (100 ml) was applied to a column of reactive green-19 resin (40 ml bed volume, equilibrated with buffer A (20 mM Hepes pH 7.0, 50 mM NaCl, 50 mM β-glycerophosphate, 1 mM DTT, 0.2 mM EDTA, 0.02% NaN$_3$ and 0.1% NP-40)). All steps were conducted on ice or at 4° C. The flow-through was discarded and the column was washed extensively with buffer A and then eluted in batch with buffer B (Buffer A supplemented with 20 mM disodium ATP, 20 mM EDTA and 0.5M NaCl, pH 7.0). Ammonium sulfate was added to the eluate to 50% (w/v) at 4° C. over the course of an hour, whereupon the suspension was centrifuged at 10,000×g for 45 minutes at 4° C. The pellet was recovered, dissolved in buffer C (Buffer A supplemented with 10 mM MnCl$_2$, pH 8.0) and desalted on Sephadex G-25 that had been equilibrated with buffer C. The desalted protein was applied to a column of Cibacron Blue 3GA agarose (Type 3000) that had been equilibrated with buffer C. The flow-through was discarded, the column was washed extensively with buffer C, and eluted in batch with buffer D (Buffer A supplemented with 20 mM EDTA and 0.15M NaCl, pH 8.0). The eluate was diluted 1:1 with buffer E (Buffer A with no added NaCl, pH 8.0) and applied to phosphocellulose that had been equilibrated with buffer F (Buffer A at pH 8.0), the phosphocellulose was washed extensively and eluted in batch with 0.6M NaCl in buffer F. The eluate was precipitated with trichloroacetic acid (10% final), washed with acetone and solubilized in SDS sample buffer. Proteins were resolved by SDS PAGE in 8% polyacrylamide, blotted to nitrocellulose and visualized with Ponceau S. The band corresponding to the autophosphorylation activity of the 90 kD kinase was excised and digested with trypsin. Tryptic peptides were resolved by HPLC and microsequenced.

Autophosphorylation of a 90 kD Kinase

Jurkat cells were treated with 50 μM forskolin for 30 minutes and nuclear extracts of forskolin-stimulated or control cells were fractionated on phosphocellulose. Proteins were separated by polyacrylamide gel electrophoresis in sodium dodecyl sulfate (SDS-PAGE), transferred to nitrocellulose, denatured in guanidine hydrochloride and assayed after renaturation. The assay revealed one major and two minor autophosphorylating kinases. The major activity, a multiplet with an apparent mobility of 90 kD (spanning 84.5–92.7 kD), was greater in extracts from forskolin-treated Jurkat cells than in extracts from control cells (FIG. 1A). Phosphocellulose chromatography resolved the multiplet into forms of slightly lower and higher apparent mobility, which we interpret to arise from differences in protein phosphorylation. The best separation and recovery of forms was obtained by eluting the column first with 0.3M NaCl and then with 1.0M NaCl.

Figures 1B, 1C:
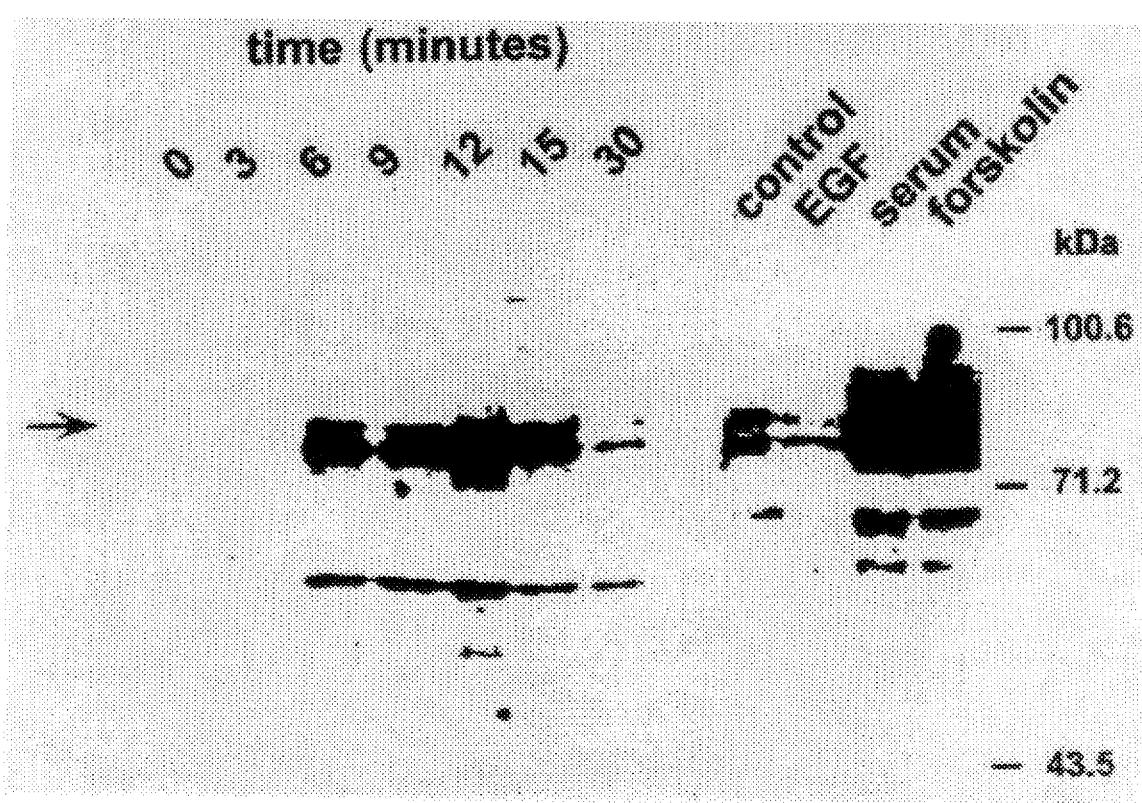
FIG. 1B: Time course of increased autophosphorylation that is induced by forskolin. Jurkat cells were stimulated with 50 µM forskolin for 0, 3, 6, 9, 12, 15, and 30 minutes. Nuclear extracts of these cells were applied to phosphocellulose. Proteins were eluted with 0.3M sodium chloride and assayed as described for FIG. 1A.
FIG. 1C: Treatments that affect 90 kD autophosphorylation in A431 cells. A431 cells were treated with epidermal growth factor (1 nM), calf serum (20%), forskolin (25 µM) or heat (42° C.) for 30 minutes. Nuclear extracts of treated cells and control cells were applied to phosphocellulose. Proteins were eluted with 1M sodium chloride and assayed as described for FIG. 1A. The 90 kD kinase is identified with an arrow.

Autophosphorylation of the species that eluted at 0.3M NaCl increased sharply within 6 minutes of stimulation and gradually declined through 30 minutes (FIG. 1B). Autophosphorylation of the species that eluted at higher salt did not respond significantly to forskolin stimulation. If extracts were prepared without the phosphatase inhibitors sodium vanadate (1 mM) and β-glycerolphosphate (50 mM) (Yu et al., 1987), or if extracts were briefly warmed to 37° C. in the presence of 5 mM magnesium chloride, the 90 kD autophosphorylation activity from stimulated cells was reduced to the levels in control cells, whereas other species (e.g., 60 kD) were unchanged. Taken together, these results indicate that this kinase is reversibly phosphorylated and increases its autophosphorylation in response to an agonist of protein kinase A.

Other agents that affect Jurkat cell metabolism, such as phytohemagglutinin, phorbol myristate acetate, calcium ionophore A23187, serum and, interleukin-2, alone or in combination, had little or no effect on the autophosphorylation activity of the 90 kD multiplet in Jurkat cells or peripheral blood lymphocytes over one hour or over four days. Other conditions, such as herpesvirus infection, heat shock, or exposure to hydrogen peroxide, sodium periodate, sodium vanadate or cadmium ion, were similarly ineffective. However, interleukin-1α treatment (CHO cells starved of serum and then treated with interleukin-1α at 10 ng/ml for 5, 10, 20, or 30 min) did result in significant stimulation of 90 kD kinase activity.

The 90 kD kinase appears to be ubiquitous, as we have found well-resolved multiplets of similar apparent molecular mass in human epithelial carcinoma (HeLa), human epidermoid carcinoma (A431), human T-cell leukemia (Jurkat), Epstein-Barr virus-transformed human B-cell (32D cl3), human T-cell lymphoma (HUT78), mouse embryo fibroblast and adipocyte (3T3-L1), mink lung (Mv1Lu), Chinese hamster ovary (CHO), African green monkey kidney (CV-1 and COS-7) cell lines, although the activities differed in their chromatographic behavior on phosphocellulose and varied slightly in their apparent mobility. Depending on the cell type, up to ten additional autophosphorylating species, with apparent molecular masses as low as >20 kD, were also detectable. It is not known whether these activities arise from transcripts of homologous genes, or whether they are unrelated to each other. In some cell lines, such as A431, an 84 kD multiplet autophosphorylation activity (78.4–89.2 kD) was both serum-inducible in serum-starved cells and forskolin-inducible, and required higher salt concentrations to elute from phosphocellulose (FIG. 1C). Neither insulin nor glucagon treatment of 3T3-L1 adipocytes increased this autophosphorylation activity, nor did forskolin or platelet-derived growth factor treatment of CHO cells, nor did fibroblast growth factor treatment of 3T3-L1 fibroblasts, nor did epidermal growth factor or heat shock treatments of A431 cells (FIG. 1C). These changes to autophosphorylation activity were remarkably stable. Major differences in activity between kinase prepared from control or stimulated cells reproducibly survived cell lysis, fractionation, boiling in SDS, gel electrophoresis, electroblotting, denaturation in guanidine hydrochloride, renaturation overnight in buffer at 4° C. and exposure to 1M sodium hydroxide.

The blotted, renatured kinases were immobilized and not in contact with potential protein substrates in solution, so only autophosphorylation was observable. These activities represent autophosphorylations, not merely binding of ATP to renatured proteins because when blots were probed in parallel with [α-$^{32}$P]ATP and [γ-$^{32}$P]ATP, only background radioactivity was associated with the membranes probed with [α-$^{32}$P]ATP, whereas discrete bands were revealed with the membranes probed with [γ-$^{32}$P]ATP. The renatured kinase required magnesium ion for activity. Blots were routinely incubated in 30 mM magnesium chloride; manganese ion, which was tested from 1 mM to 30 mM, was a poor substitute.

Physical properties of the 90 kD kinase

Figure 2:
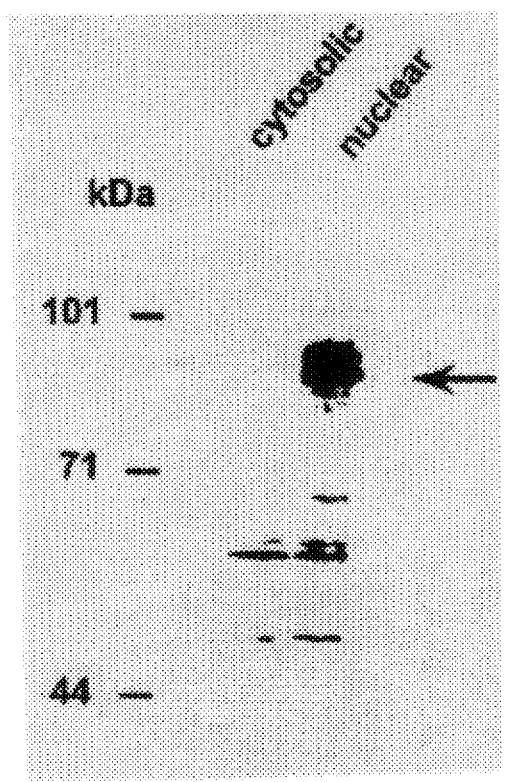
FIG. 2: The 90 kD kinase activity is localized to the nucleus in HeLa cells. A homogenate of HeLa cells was prepared in the presence of phosphatase inhibitors and centrifuged at 100,00xg for one hour at 4° C. Equal amounts of protein (50 µg) from this supernatant (the cell cytosol) and a HeLa nuclear extract were separated by gel electrophoresis and assayed as described for FIG. 1A. The 90 kD kinase is identified with an arrow.

The autophosphorylation activities present in nuclear and cytosolic extracts of HeLa cells were compared. A homogenate of HeLa cells was prepared in the presence of phosphatase inhibitors as described above and centrifuged at 100,000×g for one hour at 4° C. The protein concentration of the supernatant (S-100) was determined and equal amounts of protein from the S-100 and nuclear extract (also cleared of particulate residue) were subjected to SDS-PAGE. Proteins were electroblotted to nitrocellulose, renatured and probed with [γ-$^{32}$P]ATP. As shown in FIG. 2, an autophosphorylation signal (91.0–98.8 kD) in nuclear extract is virtually absent from cytosolic extract. Other autophosphorylation activities resolved on this blot, however, appear to be roughly equally represented in nuclear and cytosolic fractions (70.9, 64.3, 52.8 and 37.9 kD). This result suggested that the 90 kD kinase is predominantly nuclear in localization.

In vitro phosphorylation of protein and peptide substrates by the 90 kD kinase (RING3-related kinase)

Phosphocellulose-purified, renatured 90 kD kinase was tested for its substrate specificity with several different protein and peptide substrates: S6 peptide (RRLSSRA (SEQ ID NO: 14); Pelech et al., 1986), MAP kinase substrate peptide (APRTPGGRR (SEQ ID NO: 15); Sanghera et al. 1990), casein kinase II substrate (RRREEETEEE (SEQ ID NO: 16); Kuenzel and Krebs, 1985) protein kinase C serine-25 substrate (RFARKGSLRQKNV (SEQ ID NO: 17); House and Kemp, 1987), calmodulin-dependent kinase substrate (PLSRTLSVSS-NH$_2$ (SEQ ID NO: 18); Pearson et al., 1985), smooth muscle myosin light chain kinase substrate (LLRPQRATSNVFS-NH$_2$ (SEQ ID NO: 19); Kemp et al., 1983), Kemptide, a substrate for protein kinase A (LRRASLG (SEQ ID NO: 20); "Kemptide," Kemp et al., 1983), Raytide (a tyrosine kinase substrate), histones H1, H2, H2b, H3 and myelin basic protein. The results are shown in Table I:

TABLE 1

In vitro phosphorylation of peptides by renatured 90 kD kinase

| peptide substrate | [$^{32}$P]cpm | (SE) |
|---|---|---|
| none | 1205 | ±465 |
| S6 peptide | 3005 | ±535 |
| MAP kinase substrate peptide | 1443 | ±210 |
| casein kinase II peptide | 1591 | ±482 |
| protein kinase C peptide | 2056 | ±465 |
| calmodulin-dependent kinase peptide | 2330 | ±866 |
| myosin light chain kinase peptide | 58,690 | ±870 |
| Kemptide | 44,430 | ±5258 |
| Kemptide[1] | >1,000,000 | ND |
| Raytide | 4981 | ±377 |
| Raytide[2] | 322,920 | ND |

[1]Phosphorylated with the catalytic subunit of protein kinase A
[2]Phosphorylated with recombinant p43$^{v-abl}$.

The partially purified kinase phosphorylated the peptide substrates for myosin light chain kinase and protein kinase A, and myelin basic protein. Myelin basic protein is a useful in vitro substrate for MAP kinases, but the MAP kinase substrate peptide (which includes the amino acid residues that MAP kinases ordinarily phosphorylate) was not phosphorylated here. The catalytic subunit of protein kinase A was used as a positive control for Kemptide phosphorylation and recombinant p43$^{v-abl}$ was used as a positive control for Raytide phosphorylation. These results suggest that the 90 kD kinase has a narrow substrate specificity and with respect to its substrate preferences in unlike other known kinases.

Figure 4:
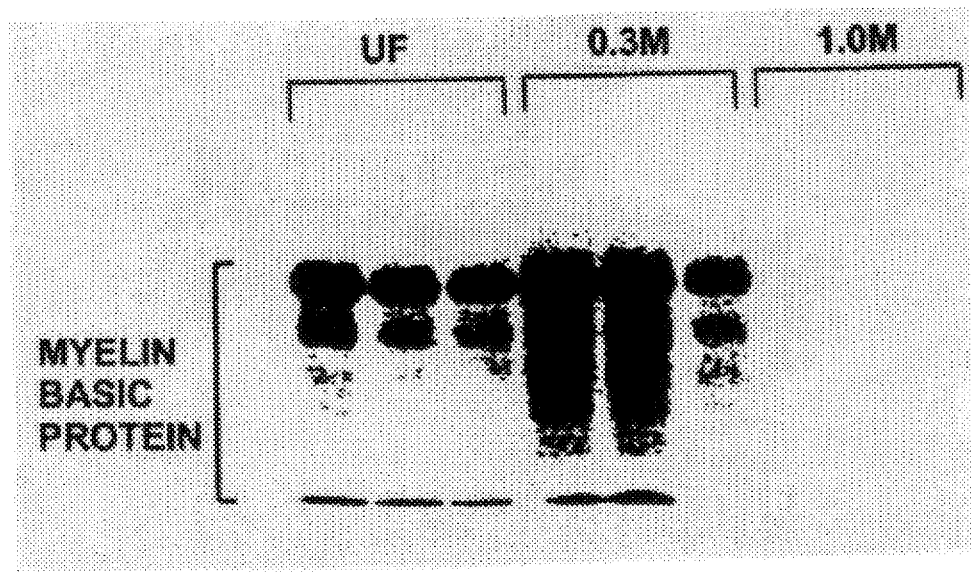
FIG. 4: Renatured 90 kD kinase was tested for its ability to phosphorylate myelin basic protein. Strips of nitrocellulose upon which the renatured kinase was immobilized were incubated in Eppendorf tubes with a solution of myelin basic protein, radioactive ATP and magnesium in buffer. After one hour at 30° C., proteins were solubilized at 100° C. in sodium dodecyl sulfate, separated by gel electrophoresis and visualized by Coomassie blue stain. An autoradiograph of phosphorylated myelin basic protein is shown in the figure. Three species of kinase were tested in triplicate: the activity in unfractionated HeLa nuclear extract (UF), the activity in a 0.3M sodium chloride fraction from phosphocellulose-fractionated HeLa nuclear extract, and the activity in a 1.0M sodium chloride fraction of the same extract.
Figure 3:
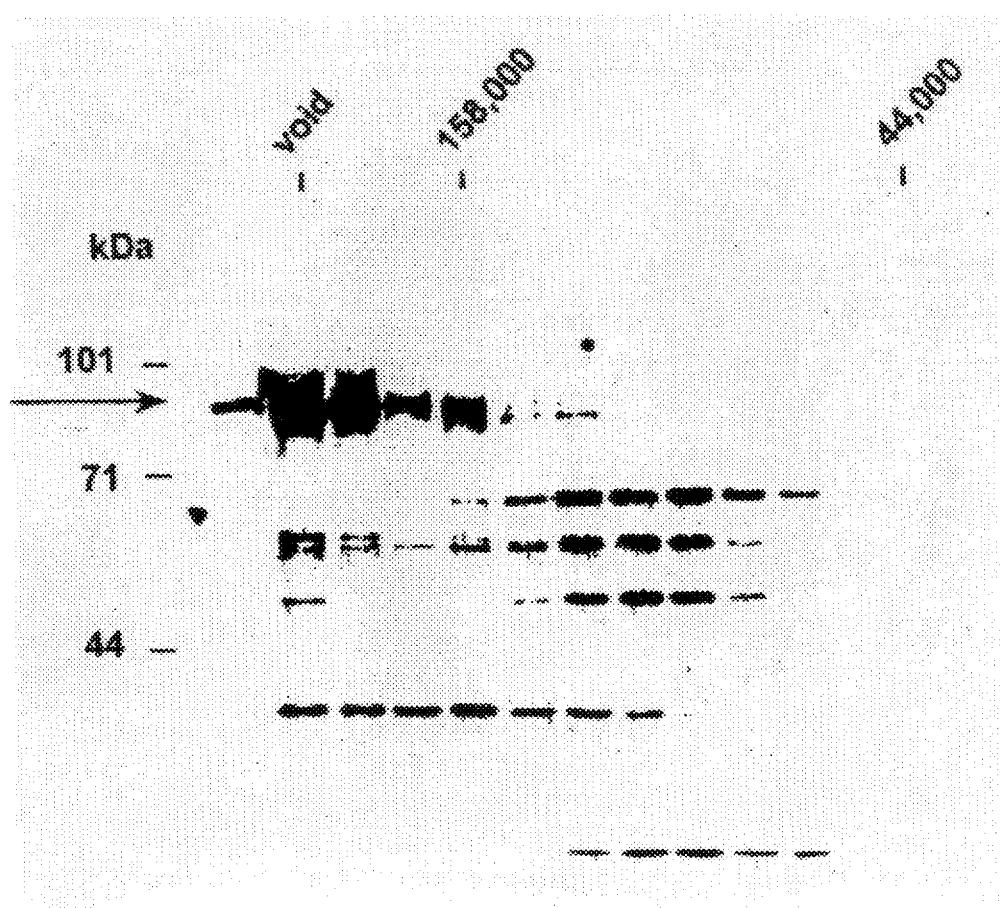
FIG. 3: The 90 kD kinase activity HeLa cells has an apparent molecular weight of 350,000 by size exclusion chromatography. Proteins in HeLa nuclear extract were separated by size exclusion chromatography at physiological ionic strength and assayed as described for FIG. 1A. The void volume of the column and molecular weight standards (for size exclusion chromatography) for immunoglobulin (158,000) and ovalbumin (44,000) are indicated above the relevant fractions, and molecular weight standards (for gel electrophoresis) are indicated to the left of the figure. The 90 kD kinase is identified with an arrow.
Figure 5A:
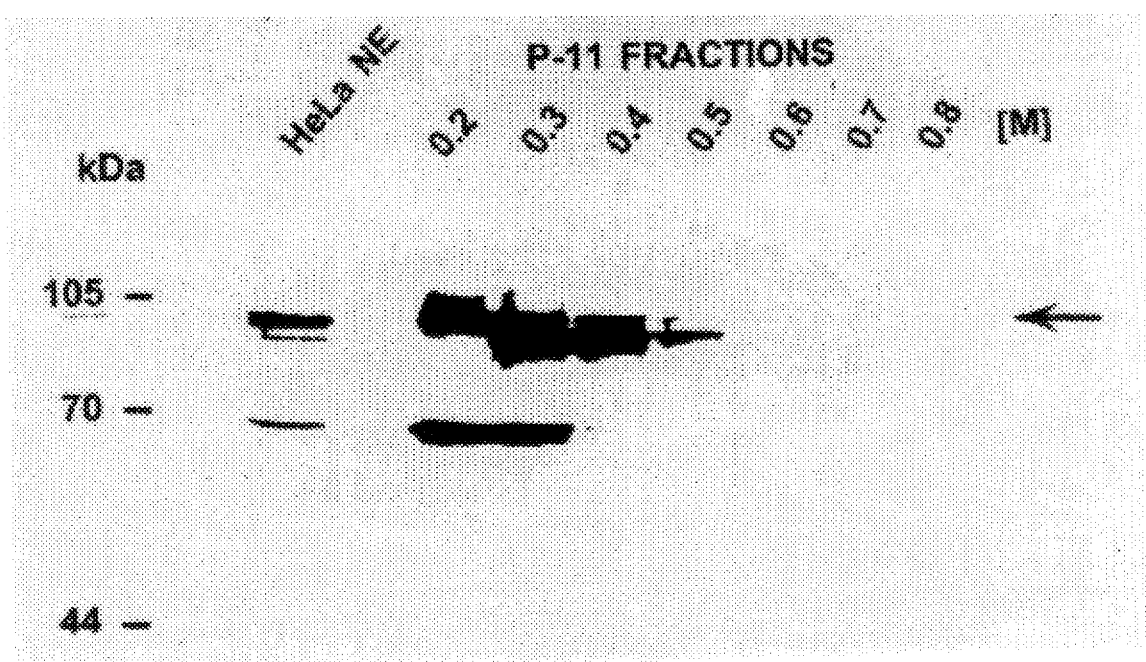
FIG. 5A: Fractionation of autophosphorylating 90 kD kinase by phosphocellulose (P-11) chromatography. HeLa nuclear extract was applied to phosphocellulose and eluted stepwise in 0.1M increments with 0.2M to 0.8M sodium chloride in buffer. Eluted proteins were assayed as described for FIG. 1A. Unfractionated nuclear extract is included for comparison at the left of the figure. Molecular weight markers are shown at the extreme left and an arrow indicates the average apparent molecular mass of the 90 kD autophosphorylating species.
Figure 7:
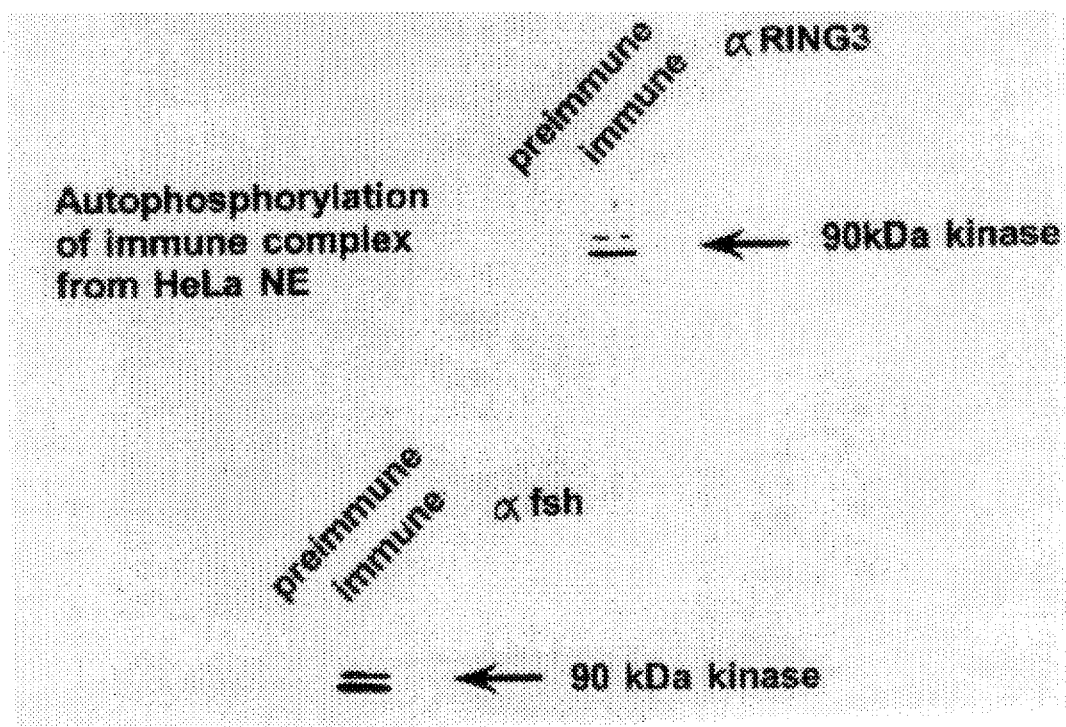
FIG. 7: Immune sera to fsh and RING3 immunoprecipitate the 90 kD autophosphorylation activity. The cDNAs for fsh and RING3 were obtained and fusions with glutathione-S-transferase (GST) were constructed. These constructs were expressed in $E.$ $coli$, the fusion proteins were purified and used to immunize rabbits. The 90 kD kinase was immunoprecipitated from HeLa nuclear extracts with these antisera and assayed by autophosphorylation as described for FIG. 1A. Pre-immune sera were not capable of immunoprecipitating this activity. Autoradiographs of 90 kD kinase renatured from immunoprecipitates of preimmune and immune sera against RING3 (above) and fsh (below) are shown.
Figure 5B:
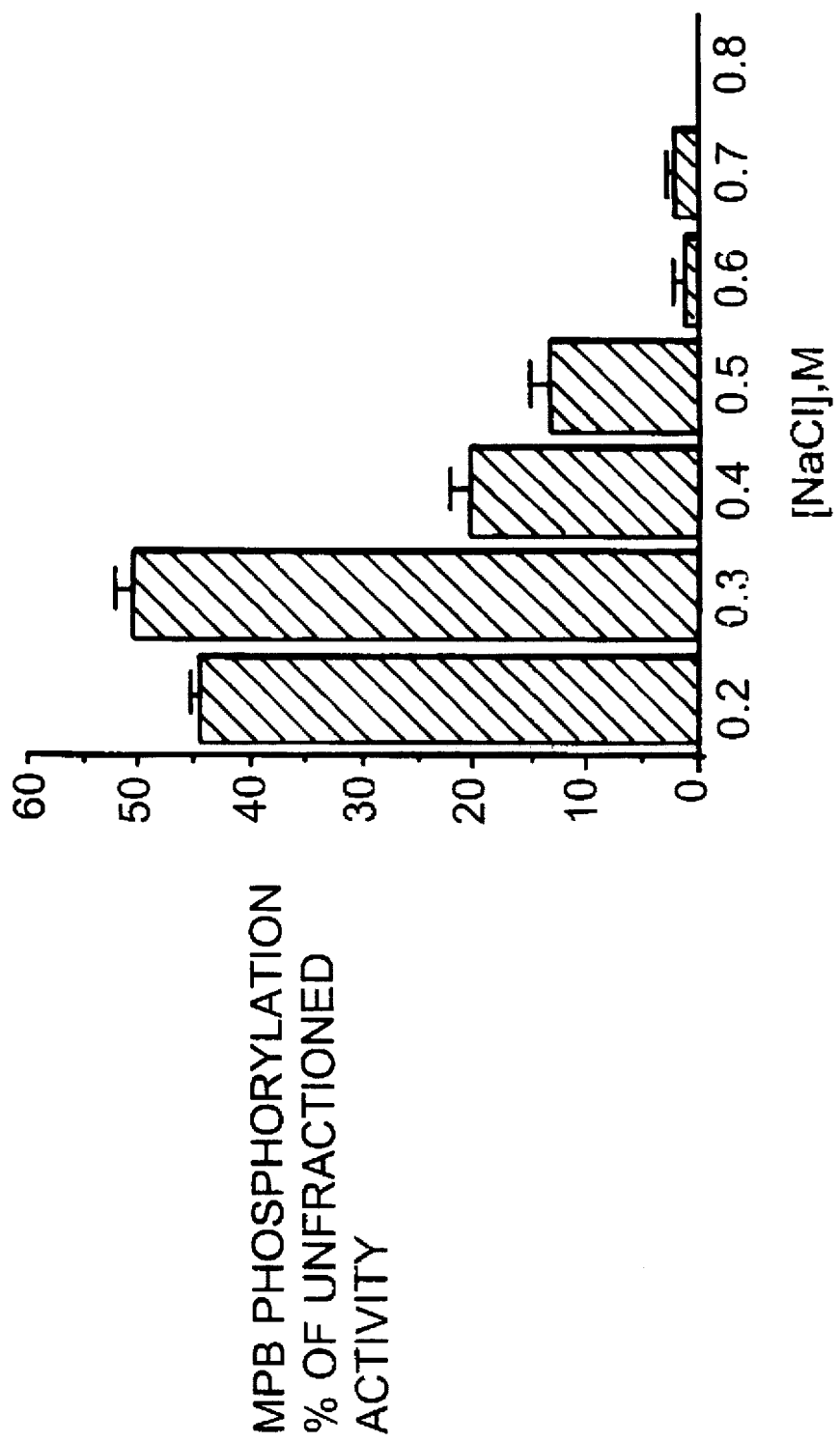
FIG. 5B: Substrate-directed phosphorylation activity of the 90 kD kinase is associated with the slower-migrating forms identified by autophosphorylation, not with the faster-migrating forms. The same fractions from FIG. 5A were renatured and used to phosphorylate myelin basic protein as described in FIG. 4.

HeLa nuclear extracts were fractionated on phosphocellulose as described. Proteins that eluted at 0.3M and 1.0M NaCl were blotted to nitrocellulose, renatured and tested for their ability to phosphorylate myelin basic protein that was supplied in solution with magnesium chloride and [γ-$^{32}$P] ATP. The kinase that eluted at the lower salt concentration, which is the inducible form in Jurkat cells and which has a slightly slower apparent mobility (FIG. 1A), showed greater substrate-directed phosphorylation activity than the species that eluted at the higher salt concentrations (FIG. 4). This result suggests that induced autophosphorylation activity is linked to increased substrate-directed phosphorylation activity. To refine this result, HeLa nuclear extract was more narrowly fractionated on phosphocellulose. Eluates were blotted to nitrocellulose and renatured either for autophosphorylation or for phosphorylation of myelin basic protein supplied in solution. Autophosphorylation of the slower mobility form was correlated with phosphorylation of myelin basic protein, whereas autophosphorylation of the faster mobility form was not (FIGS. 5A and 5B).

Without being bound by any particular theory, it appears that the 90 kD kinase is phosphorylated by a kinase to generate a hyperphosphorylated form that is the active participant in signal transduction.

Phosphoaminoacid Analysis

Figures 6A, 6B:
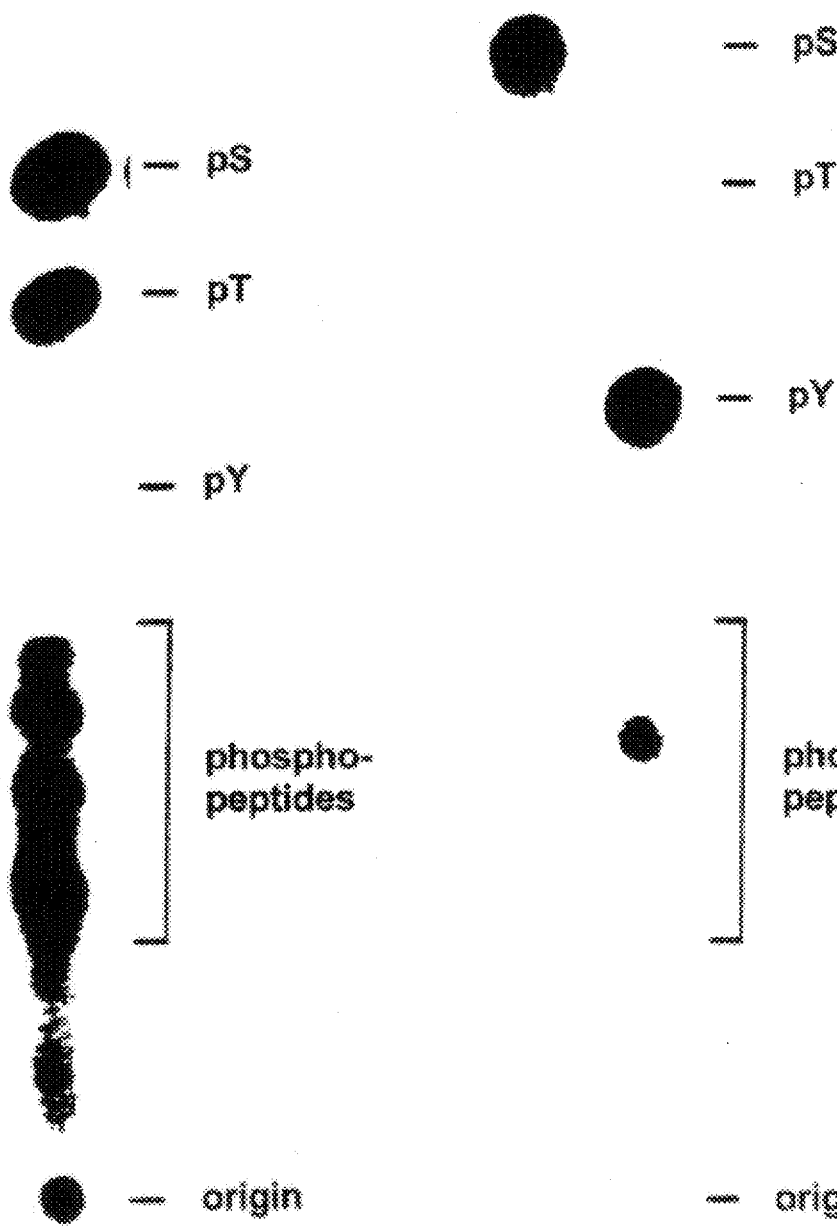
FIG. 6A: Autophosphorylated amino acids are serine and threonine, not tyrosine. HeLa nuclear extract was applied to phosphocellulose and eluted with 0.3M sodium chloride. The 90 kD kinase was isolated, renatured as described for FIG. 1A, and autophosphorylated with [γ-$^{32}$P]ATP. The radioactive kinase was then hydrolyzed in 6N hydrochloric acid and its constituent radioactive amino acids were separated by electrophoresis on silica. An autoradiograph of the silica sheet is shown. Authentic phosphoaminoacid standards were run in the same sample and visualized with ninhydrin to identify the radioactive spots.
FIG. 6B: Myelin basic protein is phosphorylated only on serine. Left side: Myelin basic protein was phosphorylated with renatured 90 kD kinase as described for FIG. 4, the hydrolyzed and separated as described for FIG. 6A. Right side: As a control for tyrosine phosphorylation, myelin basic protein was also phosphorylated in a separate reaction with recombinant p43$^{v-abl}$ protein.

The 90 kD kinase was blotted to a polyvinyldifluoride membrane and autophosphorylated with [γ-$^{32}$P]ATP. The immobilized protein was hydrolyzed in 6N HCl, and the phosphoaminoacids were separated by electrophoresis on silica. Autoradiography revealed that radioactivity was associated in equal measure with ninhydrin-visualized standards for phosphoserine (pS) and phosphothreonine (pT). No radioactivity was associated with a phosphotyrosine (pY) standard (FIG. 6A). Myelin basic protein that had been phosphorylated in vitro with renatured 90 kD kinase was solubilized in SDS and resolved by PAGE. Phosphorylated myelin basic protein was visualized with Coomassie brilliant blue, excised from the gel and acid-hydrolyzed as before. Radioactivity was associated only with pS, not with pT or pY (FIG. 6B). As a positive control for tyrosine phosphorylation, recombinant p43$^{v-abl}$ was incubated with myelin basic protein under the same conditions. In this case, pY alone was observed (FIG. 6B).

Purification and microsequencing of the 90 kD Kinase

The 90 kD nuclear kinase shares some of the characteristics of signal-transducing kinases such as pp90$^{rsk}$, pp42$^{mapk}$/pp44$^{mapk}$ and protein kinase C (Chen et al., 1992; Chung et al., 1991; Leach et al., 1989). Western blots of partially purified 90 kD kinase were probed with rabbit polyclonal antibodies to RSK, MAP kinase and protein kinase C. Protein kinase C from rat brain was used as a positive control. These antisera displayed no detectable immunoreactivity with the partially purified kinase above background.

From these results, we suspected that this 90 kD protein had not been studied previously. We therefore undertook to purify it and obtain microsequence information. HeLa nuclear extract was prepared in the presence of 50 mM β-glycerophosphate and 1 mM sodium vanadate. The autophosphorylation activity provided the assay for purification. The partially purified kinase was resolved by SDS-PAGE, blotted to nitrocellulose and digested with trypsin. Tryptic peptides were separated by HPLC and two peptides were microsequences. The first of these (DSNPDEIEIDFETLKPTTL) (SEQ ID NO: 21) was used to probe the GenBank database; a statistically significant match was obtained to the female sterile homeotic (fsh) gene of Drosophila (DROFSHB; ATCC accession number M23222, Haynes et al., 1989). There were 18/19 identities (95% match, with a S/T substitution at residue 17). A statistically significant match was also obtained with the RING3 gene of humans 9HUMRING3; ATCC accession number M80613, Beck et al., 1992) (17/19 identities (89% match) with a E/D substitution at position 5 in addition to the S/T substitution of fsh). The second peptide (AVHEQLAALSQAP) (SEQ ID NO: 22) gave a statistically significant match to RING3 (12/13 identities (92%) with a A/G substitution at position 12), but did not match fsh. The first peptide lies within the C-terminal region of highest homology between fsh and RING3, whereas the second peptide lies outside of this region, in the N-terminal direction (Beck et al., 1992). These results were surprising because neither RING3 nor fsh have been reported to be kinases. However, inspection of the protein sequence of these genes reveals several correctly spaced amino acid motifs that are consistent with the genes encoding a protein kinase (Hanks et al., 1988; Hanks, S., 1991), although of unusual organization. It was important to determine whether the gene products exhibit kinase activity.

Clones that encode the cDNAs for fsh and RING3 were obtained from the authors of the original published reports. The cDNA for fsh was a set of overlapping clones, one of which, e5.16 (Haynes et al., 1989), included the putative catalytic region of interest. This cDNA contained a site for NcoI that provided an in-frame methionine at position 785 of the open reading frame, almost 100 amino acids upstream from the putative GXGXXG (SEQ ID NO: 23), and ran through the stop codon at amino acid 1107. The fragment was fused in-frame to the 5' untranslated region of the β-globin gene and subjected to in vitro transcription/translation in both rabbit reticulocyte and wheat germ extracts as described. Products were separated by SDS- PAGE, blotted to nitrocellulose, denatured, renatured and probed with [γ-$^{32}$P]ATP as described above. No radioactivity was associated with renatured bands in excess of the signals seen in extracts primed with control viral mRNA. Several kinases in the translation reaction were capable of renaturation by this assay and may have obscured signals from the kinase in question. The fsh fragment was also expressed as a histidine-tagged protein, a T7 antibody-tagged protein and as a glutathione-S-transferase (GST) fusion protein. The bacterially expressed fusion protein showed little or no activity. The same was true for fusion constructs of RING3, with had a convenient NcoI site to yield an in-frame methionine at amino acid 347 of the open reading frame, just over 200 residues upstream from the putative GXGXXG (SEQ ID NO: 23) and continued through the run of serines to the stop codon at 755. The failure of these bacterially translated cDNAs to demonstrate kinase activity in vitro can probably be ascribed to the usual shortcomings with post-translational processing in prokaryotes.

Recombinant RING3 protein was incubated with HeLa nuclear extract and ATP, repurified and assayed again. The protein now possessed kinase activity. This result implies the existence of a kinase in nuclear extract. For mammalian overexpression, COS cells were transiently transfected with a CMV expression vector carrying RING3 cDNA. Nuclear extracts were prepared from these transfected cells and fractionated by phosphocellulose chromatography, which we found could resolve ectopically-expressed from endogenous kinase activity. We believe that the distinct chromatographic behavior of ectopic and endogenous kinase is due to differences in their phosphorylation. These results strongly suggest that RING3 cDNA encodes renaturable 90 kDa nuclear kinase activity.

For these studies, RING3 cDNA (clone CEM32, a 4 kb insert in CDM8; Beck et al., 1992) was propagated in MC1061/P3 (Invitrogen). An NcoI-EcoRI fragment (nucleotides 2214–3640) was excised from RING3 and ligated into the BamHI and EcoRI sites of pGEX-2T for overexpression (Lin and Green, 1991). Rabbit polyclonal antibody was raised against purified GST fusion protein. For production of purified antibody, rabbit immune sera were incubated with GST-agarose to remove antibodies against GST epitopes. Polyclonal antibodies against RING3 epitopes were then purified by antigen affinity chromatography on Affigel columns of the purified GST fusion protein.

For construction of a eukaryotic overexpression vector, RING3 cDNA was obtained by double-stranded polymerase chain reaction (PCR) amplification of clone CEM32 with a forward primer (5'-CGCCGCGGATCCATGGCT TCGGTGCCTGCT-3') (SEQ ID NO: 24) that engineered a 5' BamHI site at the amino-terminal methionine of the coding sequence and a reverse primer (5'-GGCTGGGAATTCAATGTT-3') (SEQ ID NO: 25) that employed a native EcoRI site in the 3' untranslated region. The BamHI-EcoRI fragment from PCR was ligated into the BamHI and EcoRI sites in the multicloning site of pcDNA(I) (Invitrogen). For construction of a bacterial overexpression vector, the BamHI-EcoRI fragment was ligated in-frame into the same sites of RSETA (Invitrogen), to fuse six histidines to the N-terminus of RING3. Clones were verified by dideoxy sequencing. Histidine-tagged recombinant protein was purified on Ni$^+$-agarose (Qiagen), and phosphorylated by incubation for 30 min at 30° C. with HeLa nuclear extract in Buffer A that contained with 10 mM ATP and 5 mM MgCl$_2$ but no Na vanadate. Phosphorylated protein was repurified on Ni$^+$-agarose and assayed by in-gel kinase assay (Gotoh et al., 1990).

The GST fusion proteins with the fsh and RING3 fragments were purified from lysates of induced bacteria, purified on glutathione agarose and injected into rabbits for the production of antibody. The fusion constructs were of the correct electrophoretic mobility on SDS gels. Immune sera were screened for the ability to immunoprecipitate the original kinase activity from HeLa nuclear extract. Both immune sera to GST-fsh and to GST-RING3 immunoprecipitated the renaturable autophosphorylation activity with apparent molecular weight 90 kD, whereas none of the preimmune sera immunoprecipitated this activity. This result strongly supports the interpretation that fsh and RING3 are kinases, and that the microsequenced peptides are derived from a HeLa gene product that is homologous to the Drosophila and human T-cell cDNAs.

Figure 8:
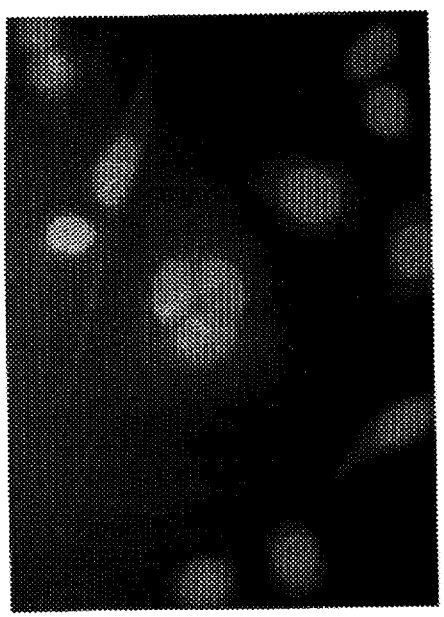
FIG. 8: Immunofluorescence with antibodies against RING3 confirm nuclear localization of 90 kD kinase in HeLa cells. HeLa cells were grown on coverslips and fixed by standard methods. Coverslips were incubated with pre-immune serum or with affinity-purified antibodies against GST fusion proteins of RING3 or fsh. Goat anti-rabbit secondary antibodies conjugated to fluorescein were used to visualize the primary antibodies.

Rabbit immune sera were incubated with GST-agarose to remove antibodies against GST epitopes. Polyclonal antibodies against RING3 and fsh epitopes were then purified by antigen affinity chromatography on Affigel columns of each purified GST fusion protein. Purified antibodies were assayed by immunoblot. Indirect immunofluorescence of HeLa cells with purified polyclonal antibody and with fluorescein-conjugated second antibody shows that RING3 is localized to the nucleus (FIG. 8). This result is in agreement with FIG. 2, which suggested that the kinase is exclusively nuclear, and with the presence of a putative nuclear localization signal in the open reading frame of the RING3 cDNA. Antibody was excluded from nucleoli, consistent with patterns of nuclear staining for proteins that are involved in transcription.

EXAMPLE 2

Biochemical Assay for Leukemia

The above-described assay (FIG. 1A) for 90 kD kinase activity can be used to diagnose leukemia. The following experiment is one example of a suitable diagnostic assay.

Figures 9A, 9B:
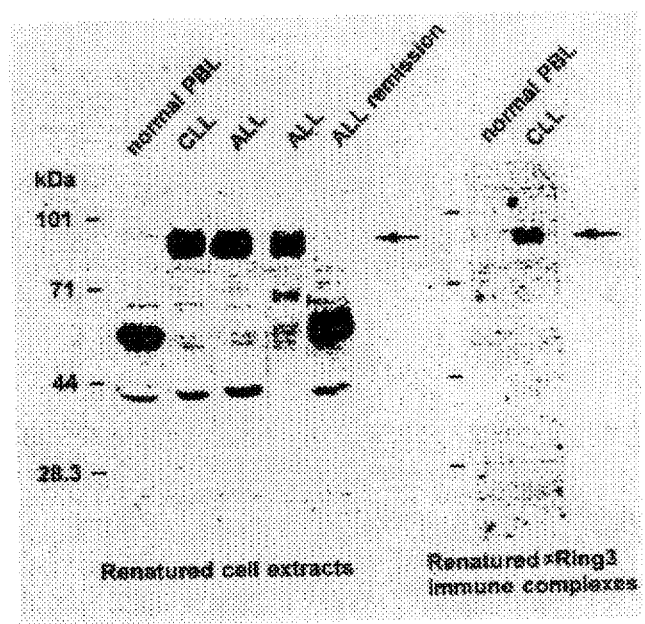
FIG. 9A: Autophosphorylation activity of the 90 kD kinase is increased in patients suffering from leukemia, but not in normal patients or leukemia patients in remission. The position of molecular weight markers is shown at the left. The position of the 90 kD kinase is indicated by the arrow.
FIG. 9B: Anti-RING3 antibody immunoprecipitates 90 kD kinase autophosphorylation activity from leukemic patients. The position of molecular weight markers is shown at the left. The position of the 90 kD kinase is indicated by the arrow.

For each patient assayed cell extracts were prepared from 10$^7$ PBLS. The proteins were separated by SDS-PAGE, renatured and assayed for 90 kD kinase autophosphorylation activity as described above (FIG. 1A). The results of this analysis are presented in FIG. 9A. The following patients were used: a normal 34 year-old male (lane 1); a 69 year-old male diagnosed with chronic lymphocytic leukemia (>10$^6$ mature T-cells/µl, lymphostasis, immune suppression) (lane 2); a 4 year-old female diagnosed with acute lymphocytic leukemia in proliferative blast stage (lane 3); a 15 year-old male diagnosed with acute lymphocytic leukemia in proliferative blast stage (lane 4); the same 15 year-old male after chemotherapy (lane 5). The results show that there is significant 90 kD kinase activity in sample from patients with active leukemia, but not in normal patients or those in remission. These results are representative of ten normal controls and ten acute lymphocytic leukemia patients (>50, 000 blasts/µl in each case) and ten normal control patients.

These results demonstrate that 90 kD kinase activity can be used to diagnose leukemia and detect the presence of leukemic cells. While 90 kD kinase activity was increased in acute lymphocytic leukemia patients, the expression of the 90 kD kinase, as determined by immunoblotting with anti-RING3 antibody, was approximately the same in acute lymphocytic leukemia patients and normal controls.

The level of 90 kD kinase activity may be used as an indication of the stage of leukemic progression. Vonken et al. (1992) and Griffiths et al. (1992) describe a murine model of leukemia which permits study of early stages of leukemia as well as its progression. This model is useful for adapting 90 kD kinase activity assays for monitoring disease progression. By measuring the activity of 90 kD kinase it is possible to determine the degree of disease progression.

As an alternative method for measuring 90 kD kinase, anti-RING3 antibody can be used to precipitate 90 kD kinase. The immune complexes are then washed, solubilized with SDS and autophosphorylation is assayed as described above.

When autophosphorylation activity was measured in cell extract, a prominent 50 kD band was observed in the samples taken from the normal control and the patient in remission, but not the leukemic patients. The absence of activity might be able to serve as an additional indication of a leukemic condition.

Assays for 90 kD Kinase Activity

Any means for measuring the activity of the 90 kD kinase can be used as an assay for leukemia. In addition to the assays described above and in FIGS. 1A, 9A and 9B, the level of 90 kD kinase activity can be determined by measuring the phosphorylation of a natural or synthetic 90 kD kinase substrate. For example, an ELISA-based assay can be used. In one such assay substrate peptide, immobilized on a solid support, is incubated with a 90 kD kinase-containing sample (a crude extract or a partially purified sample) in the presence of ATP (added if needed). Phosphorylated substrate is then detected by an antibody which binds the phosphorylated, but not the non-phosphorylated, substrate followed by treatment with an enzyme-conjugated secondary antibody and enzyme substrate.

It should be understood that it may not be necessary to carry out an autophosphorylation reaction in order to detect active 90 kD kinase. The 90 kD kinase in the leukemic (or pre-leukemic) cells may be substantially autophosphorylated.

In an alternative assay, 90 kD kinase in a test sample is substantially or partially purified by immunoprecipitation using an anti-90 kD kinase antibody. Substrate and [$\gamma^{32}$P]-ATP (or other appropriate label) are then incubated with the partially purified 90 kD kinase in an appropriate buffer (generally containing ATP, DTT, MgCl$_2$, and other components). An aliquot of the reaction mixture is transferred to a solid support (e.g., a phosphocellulose filter) and the radioactivity is detected after washing (e.g., with 1% phosphoric acid) to remove free [$\gamma^{32}$P]-ATP.

In any assay it is important to eliminate other kinases which might significantly interfere with the ability to detect phosphorylation by the 90 kD kinase. Interference can be avoided by employing a substrate which is not significantly phosphorylated by other kinase present in the sample (e.g., the cell extract). Alternatively, the 90 kD kinase present in the sample can be partially purified to substantially eliminate interfering kinases. This purification can be accomplished by any standard procedure, including affinity purification with antibodies selective for the 90 kD kinase (or RING3). For purposes of partial or complete purification it is not required that the anti-90 kD antibody be selective for the autophosphorylated form of the 90 kD kinase.

Anti-90 kD kinase Antibodies

Human 90 kD kinase (or immunogenic fragments or analogues) may be used to raise antibodies useful in the invention; such polypeptides may be produced by recombinant or peptide synthetic techniques (see, e.g., *Solid Phase Peptide Synthesis*, infra; Ausubel et al., 1994). The peptides may be coupled to a carrier protein, such as KLH as described in Ausubel et al., 1994. The KLH-peptide is mixed with Freund's adjuvant and injected into guinea pigs, rats, or preferably rabbits. Antibodies may be purified by peptide antigen affinity chromatography.

Monoclonal antibodies may also be prepared using the 90 kD kinases described above and standard hybridoma technology (see, e.g., Kohler et al., 1975; Kohler et al., 1976a; Kohler et al., 1976b; Hammerling et al., 1981; Ausubel et al., 1994).

Once produced, polyclonal or monoclonal antibodies are tested for specific 90 kD kinase recognition by Western blot or immunoprecipitation analysis (by the methods described in Ausubel et al., 1994). Antibodies which specifically recognize the 90 kD kinase are considered to be useful in the invention; such antibodies may be used, e.g., in an immunoassay to monitor the level of 90 kD kinase produced by a mammal (for example, to determine the amount or subcellular location of 90 kD kinase).

Preferably, antibodies of the invention are produced using fragments of the 90 kD kinase which appear likely to be antigenic, by criteria such as high frequency of charged residues. In one specific example, such fragments are generated by standard techniques of PCR and cloned into the pGEX expression vector (Ausubel et al., 1994). Fusion proteins are expressed in *E. coli* and purified using a glutathione agarose affinity matrix as described in Ausubel, et al., 1994). To attempt to minimize the potential problems of low affinity or specificity of antisera, two or three such fusions are generated for each protein, and each fusion is injected into at least two rabbits. Antisera are raised by injections in a series, preferably including at least three booster injections.

Antisera is cleared of anti-GST antibodies using GST immobilized on a glutathione column, and the antisera are checked by ELISA for titer and specificity, using GST fusion proteins as controls. Antisera is also checked for its ability to immunoprecipitate in vitro translated 90 kD kinases or control proteins, such as glucocorticoid receptor, CAT, or luciferase. Western blots of total or nuclear versus cytoplasmic fractionated HeLa cell proteins are also probed with the antisera to assess specificity and to characterize subcellular compartmentalization. In these and other immunologic assays, specificity is confirmed by the specific competition with the GST fusion protein.

Once the specificity of an antiserum is confirmed, it may be used in any standard indirect immunofluorescence procedure to determine the amount or subcellular distribution of 90 kD kinase in a particular cell type.

In many applications anti-RING3 antibodies, produced as described herein or by other standard techniques may be useful for in the methods of the invention for the same purposes as anti-90 kD kinase antibodies.

Anti-90 kD Kinase Antibodies Specific for Autophosphorylated 90 kD Kinase

Antibodies which are selective for the phosphorylated form of 90 kD kinase (particularly the form created by autophosphorylation) are particularly useful. To be useful in diagnostic assays, the antibody must be selective for the site where autophosphorylation occurs. This is because the 90 kD kinase may be phosphorylated by other kinases. Antibodies which recognize these phosphorylation sites that are not autophosphorylation sites are far less likely to be useful for detecting activated 90 kD kinase.

Appropriate antibodies will not substantially bind non-autophosphorylated forms of 90 kD kinase. Such antibodies can be prepared by immunization with the appropriate phosphopeptide derived from the 90 kD kinase (or RING3). A suitable phosphopeptide can be prepared by digesting phosphorylated protein and then isolating and purifying one or more suitable phosphorylated polypeptides, which peptides were created by autophosphorylation. Alternatively, a synthetic peptide based on the phosphorylation site of the 90 kD kinase (or RING3) can be phosphorylated in vitro, e.g., by the 90 kD kinase (or other kinase which phosphorylates the relevant site, e.g., protein kinase C or casein kinase II or protein kinase A may phosphorylate the relevant site on the 90 kD kinase), and then used for immunization. The generation of antibodies which selectively bind the autophosphorylated, but not the non-autophosphorylated form of the 90 kD kinase can be carried out according to procedures similar to those which have been used by others to prepare other phosphoprotein selective antibodies. For example, Ginty et al. (1993) describes the creation of a polyclonal antibody which selectively binds the phosphorylated, but not the non-phosphorylated, form of rat cyclic AMP response element binding protein.

Antibodies which are selective for active (or inactive) 90 kD kinase may be used in any standard immunoassay format (e.g., ELISA, Western blot, or RIA assay) to measure 90 kD kinase polypeptide levels; again comparison would be to normal levels of active (or inactive) 90 kD kinase, and a change (increase) in 90 kD kinase expression or activation would be indicative of a leukemic or pre-leukemic condition. Examples of immunoassays are described, e.g., in Ausubel et al., 1994. Immunohistochemical techniques may also be utilized for 90 kD kinase detection. For example, a tissue sample may be obtained from a patient, and a section stained for the presence of 90 kD kinase using an anti-90 kD kinase antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. 1994).

Identification of Molecules that Modulate 90 kD Kinase Expression or Activity identification of the 90 kD kinase facilitates the identification of molecules which increase or decrease its expression or activity. According to one approach, candidate molecules (e.g., peptide or non-peptide molecules found, e.g., in a cell extract, mammalian serum, or growth medium on which mammalian cells have been cultured or as a part of a small molecule screening library) are added at varying concentrations to the culture medium of cells (e.g., HeLa or COS cells) which express 90 kD kinase mRNA. Expression of the 90 kD kinase is then measured by standard Northern blot analysis (Ausubel et al., 1994) using a 90 kD kinase (or RING3) cDNA (or cDNA fragment) as a hybridization probe. The level of 90 kD kinase expression in the presence of the candidate molecule is compared to the level measured for the same cells in the same culture medium but in the absence of the candidate molecule. Alternatively, activity of the 90 kD kinase may be measured (e.g., using one of the assays described herein). The level of 90 kD kinase activity in the presence of the candidate molecule is compared to the level measured for the same cells in the same culture medium but in the absence of the candidate molecule.

Candidate modulators may be purified (or substantially purified) molecules or may be one component of a mixture of compounds (e.g., an extract or supernatant obtained from cells; Ausubel et al., 1994). In a mixed assay, 90 kD kinase expression (or activity) is tested against progressively smaller subsets of the candidate compound pool (e.g., produced by standard purification techniques, e.g., HPLC or FPLC) until a single compound is finally demonstrated to modulate the the 90 kD kinase activity. Candidate 90 kD kinase modulators include peptide as well as non-peptide molecules.

90 kD kinase Expression

In general, 90 kD kinase according to the invention may be produced by transformation of a suitable host cell (e.g., COS cells or HeLa cells) with all or part of a 90 kD kinase-encoding cDNA fragment in a suitable expression vehicle.

Those skilled in the field of molecular biology will understand that any of a wide variety of expression systems may be used to provide the recombinant protein. The precise host cell used is not critical to the invention. The 90 kD kinase may be produced in a prokaryotic host (e.g., *E. coli*) or in a eukaryotic host (e.g., *Saccharomyces cerevisiae* or mammalian cells, e.g., COS 1, NIH 3T3, or HeLa cells). Such cells are available from a wide range of sources (e.g., the American Type Culture Collection, Rockland, Md.; also, see, e.g., Ausubel et al., 1994). The method of transformation or transfection and the choice of expression vehicle will depend on the host system selected. Transformation and transfection methods are described, e.g., in Ausubel et al., supra; expression vehicles may be chosen from those provided, e.g., in *Cloning Vectors*: A Laboratory Manual (Pouwels et al., 1985, Supp. 1987).

Other suitable expression systems include Baculovirus and Vaccinia virus systems as described, e.g., in Ausubel et al., supra.

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a 90 kD kinase would be inserted into the pMAMneo vector in an orientation designed to allow expression. The recombinant 90 kD kinase would be isolated as described below. Other preferable host cells which may be used in conjunction with the pMAMneo expression vehicle include COS cells and CHO cells (ATCC Accession Nos. CRL 1650 and CCL 61, respectively). Cytomegalovirus promoter-based expression systems may also be useful.

Alternatively, the 90 kD kinase can be produced by a stably-transfected mammalian cell line. A number of vectors suitable for stable transfection of mammalian cells are available to the public, e.g., see Pouwels et al., supra; methods for constructing such cell lines are also publicly available, e.g., in Ausubel et al., 1994. In one example, cDNA encoding the 90 kD kinase is cloned into an expression vector which includes the dihydrofolate reductase (DHFR) gene. Integration of the plasmid and, therefore, the 90 kD kinase-encoding gene into the host cell chromosome is selected for by inclusion of 0.01–300 µM methotrexate in the cell culture medium (as described in Ausubel et al., 1994). This dominant selection can be accomplished in most cell types. Recombinant protein expression can be increased by DHFR-mediated amplification of the transfected gene. Methods for selecting cell lines bearing gene amplifications are described in Ausubel et al., 1994; such methods generally involve extended culture in medium containing gradually increasing levels of methotrexate. DHFR-containing expression vectors commonly used for this purpose include pCVSEII-DHFR and pAdD26SV(A) (described in Ausubel et al., 1994). Any of the host cells described above or, preferably, a DHFR-deficient CHO cell line (e.g., CHO DHFR-cells, ATCC Accession No. CRL 9096) are among the host cells preferred for DHFR selection of a stably-transfected cell line or DHFR-mediated gene amplification.

Once the recombinant 90 kD kinase is expressed, it is isolated, e.g., using affinity chromatography. In one example, an anti-90 kD kinase antibody (e.g., produced as described herein) may be attached to a column and used to isolate the 90 kD kinase. Lysis and fractionation of 90 kD kinase-harboring cells prior to affinity chromatography may be performed by standard methods (see, e.g., Ausubel et al., 1994). Alternatively, a 90 kD kinase fusion protein, for example, a 90 kD kinase-maltose binding protein, a 90 kD kinase-β-galactosidase, or a 90 kD kinase-trpE fusion protein, may be constructed and used for 90 kD kinase isolation (see, e.g., Ausubel et al., 1994; New England Biolabs, Beverly, Mass.).

Once isolated, the recombinant protein can, if desired, be further purified, e.g., by high performance liquid chromatography (see, e.g., Fisher, Laboratory *Techniques In Biochemistry And Molecular Biology*, eds., Work and Burdon, Elsevier, 1980).

Polypeptides of the invention, particularly short 90 kD kinase fragments, can also be produced by chemical synthesis (e.g., by the methods described in *Solid Phase Peptide Synthesis*, 2nd ed., 1984, The Pierce Chemical Co., Rockford, Ill.).

These general techniques of polypeptide expression and purification can also be used to produce and isolate useful fragments or analogs of the 90 kD kinase (described herein).

Other Embodiments

In other embodiments, the invention includes a substantially pure preparation of 90 kD kinase. Preferably, the 90 kD kinase includes an amino acid sequence substantially identical to that of human 90 kD kinase.

The invention also features purified DNA (for example, cDNA) which includes a sequence encoding a 90 kD kinase, preferably encoding a human 90 kD kinase; a vector and a cell which includes a purified DNA of the invention; and a method of producing a recombinant 90 kD kinase involving providing a cell transformed with DNA encoding 90 kD kinase positioned for expression in the cell, culturing the transformed cell under conditions for expressing the DNA, and isolating the recombinant 90 kD kinase. The invention further features recombinant 90 kD kinase produced by such expression of a purified DNA of the invention.

By "90 kD kinase polypeptide" is meant a polypeptide which can autophosphorylate and is homologous to a polypeptide fragment of the 90 kD kinase. Preferably, such a polypeptide has an amino acid sequence which is most preferably 95% or even 99% identical to the amino acid sequence of human 90 kD kinase.

For polypeptides, the length of comparison sequences will generally be at least 20 amino acids, preferably at least 30 amino acids, more preferably at least 50 amino acids, and most preferably 100 amino acids.

Homology is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "protein" and "polypeptide" is meant any chain of amino acids, regardless of length or post-translational modification (e.g., glycosylation or phosphorylation).

By "substantially pure" is meant a preparation which is at least 60% by weight (dry weight) the compound of interest, i.e., a 90 kD kinase. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). Preferably, such a sequence is at least 90%, more preferably 95%, and most preferably 99% identical at the amino acid level to the sequence human 90 kD kinase. For nucleic acids, the length of comparison sequences will generally be at least 50 nucleotides, preferably at least 60 nucleotides, more preferably at least 75 nucleotides, and most preferably 110 nucleotides. A "substantially identical" nucleic acid sequence codes for a substantially identical amino acid sequence as defined above.

By "transformed cell" is meant a cell into which (or into an ancestor of which) has been introduced, by means of recombinant DNA techniques, a DNA molecule encoding (as used herein) 90 kD kinase.

By "positioned for expression" is meant that the DNA molecule is positioned adjacent to a DNA sequence which directs transcription and translation of the sequence (i.e., facilitates the production of 90 kD kinase).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody.

By "specifically binds" is meant an antibody which recognizes and binds 90 kD kinase but which does not substantially recognize and bind other molecules in a sample, e.g., a biological sample, which naturally includes 90 kD kinase.

In another aspect the invention relates to a method for regulating transcription of a gene of interest. The method comprises modulating the activity of a kinase that activates transcription of the gene and is (i) substantially exclusively intranuclearly localized; (ii) capable of autophosphorylation; (iii) selectively bindable with antibodies raised against the RING3 portion of GST-RING3; (iv) of a molecular weight of from about 82.5 to about 92.7 kilodaltons; and (v) includes peptide sequences Asp-Ser-Asn-Pro-Asp-Glu-Ile-Glu-Ile-Asp-Phe-Glu-Thr-Leu-Lys-Pro-Thr-Thr-Leu (SEQ ID NO: 1) and Ala-Val-His-Glu-Gln-Leu-Ala-Ala-Leu-Ser-Gln-Ala-Pro (SEQ ID NO: 2).

In this aspect, modulating the kinase activity can comprise stimulating the phosphorylation activity of the kinase, so as to prevent inappropriate transcription of a regulated gene of interest. More particularly, the kinase activates a transcription factor for initiating transcription of the gene of interest. Alternatively, modulating the kinase activity can comprise inhibiting the phosphorylation activity of the kinase so as to inhibit the transcription of the gene of interest. More particularly, the kinase activates a transcription factor for the gene of interest.

Another aspect of the invention provides a method for regulating the transcription of a gene of interest in a cell which comprises contacting said cell with a compound that specifically binds with a cell surface receptor so as to modulate by signal transduction the activity of a kinase that: (i) is substantially exclusively intranuclearly localized; (ii) is capable of autophosphorylation; (iii) is selectively bindable with antibodies raised against the RING3 portion of GST-RING3; (iv) has a molecular weight of from about 82.5 to about 92.7 kilodaltons; and (v) includes peptide sequences Asp-Ser-Asn-Pro-Asp-Glu-Ile-Glu-Ile-Asp-Phe-Glu-Thr-Leu-Lys-Pro-Thr-Thr-Leu (SEQ ID NO: 1) and Ala-Val-His-Glu-Gln-Leu-Ala-Ala-Leu-Ser-Gln-Ala-Pro (SEQ ID NO: 2). In this aspect, the compound stimulates a cell surface receptor including those from the group consisting of peptide growth factor receptors, steroid and other hormone receptors, ion channel receptors, serpentine cell surface receptors and immunophilins. This aspect also relates to stimulating the signal transduction function of said kinase by contacting said cell with forskolin or analog or derivation thereof.

Also, lectin-binding receptors, antibody/antigen receptors, cell contact receptors that are otherwise involved in self/non-self or immune recognition or that are encoded by the major histocompatibility complex, cell adhesion receptors, steroid and other hormone receptors, chemotactic receptors and receptors for biochemical molecules, which molecules are involved in signal transduction.

In this aspect, regulating can comprise stimulating the phosphorylation activity of the kinase so as to either induce transcription or prevent inhibition of transcription of the gene of interest. Alternatively this aspect can include a method for inhibiting the phosphorylation activity of the kinase.

Another aspect of the invention provides a recombinant method of regulating transcription of a gene of interest. In this aspect, the transcription of a gene downstream or even upstream in a signal transduction pathway from the kinase of the invention is regulated by an expressible gene construct comprising a promoter and a structural gene sequence for the kinase of the invention or a protein that affects the activity of the kinase that is introduced into the cell where transcription is to be regulated.

Another aspect of the invention relates to new nuclear kinases that are regulated by signal transduction and that participate in phosphorylation cascades which regulate transcription and related methods for regulating transcription. The kinases are: (i) substantially exclusively intranuclearly localized; (ii) capable of autophosphorylation; (iii) selectively bindable with antibodies raised against the RING3 portion of GST-RING3; (iv) of a molecular weight of from about 82.5 to about 92.7 kilodaltons; and (v) include peptide sequences Asp-Ser-Asn-Pro-Asp-Glu-Ile-Glu-Ile-Asp-Phe-Glu-Thr-Leu-Lys-Pro-Thr-Thr-Leu (SEQ ID NO: 1) and Ala-Val-His-Glu-Gln-Leu-Ala-Ala-Leu-Ser-Gln-Ala-Pro (SEQ ID NO: 2). Also contemplated are biologically active fragment derivatives, analogs, conjugates, and fusion proteins thereof.

As another aspect of the invention, protein kinase activity has now been discovered for RING3 (human). RING3 is attributed with a role consistent with that of the novel kinases.

Another aspect of the invention relates to the recognition of the relevance of the novel kinases(s) of the invention and RING3 to (i) the regulation or control of the cell cycle, (ii) control of cell differentiation, and (iii) control of cell growth and metabolism.

In another aspect, the invention features gene therapy employing DNA encoding the 90 kD kinase (or RING3). Where overexpression or overactivation of the 90 kD kinase is associated with a disease state, an antisense RNA product encoding all or part of the 90 kD kinase may be used to reduce expression of the 90 kD kinase. The antisense RNA by be administered, for example, by expression from a retroviral vector delivered, for example, to the bone marrow. Treatment may be combined with more traditional cancer therapies such as surgery, radiation, or other forms of chemotherapy. In other disease states it may be desirable to increase expression of the 90 kD kinase. For example, in AIDS patients it may be desirable to increase proliferation of certain classes of lymphocytes (e.g. CD4+ cells). Introduction of a gene expressing (or overexpressing) active 90 kD kinase into CD4+ cells by gene therapy may increase proliferation of these cells. For example, CD4+ cells could be withdrawn from a patient and treated to remove all traces of HIV. The cells would then be transfected with a virus encoding 90 kD kinase. The CD4+ cells would then be reintroduced into the patient.

In other embodiments, the invention includes proteins which are substantially identical to a human 90 kD kinase such homologs include other substantially pure naturally occurring mammalian 90 kD kinases as well as allelic variants; natural mutants; induced mutants; proteins encoded by DNA that hybridizes to the 90 kD kinase DNA sequence under high stringency conditions or low stringency conditions (e.g., washing at 2×SSC at 40° C. with a probe length of at least 40 nucleotides); and polypeptides or proteins specifically bound by antisera directed to a 90 kD kinase. The term also includes chimeric polypeptides that include a 90 kD kinase fragment.

The invention further includes analogs of any naturally occurring 90 kD kinase. Analogs can differ from the naturally occurring 90 kD kinase by amino acid sequence differences, by post-translational modifications, or by both. Analogs of the invention will generally exhibit at least 85%, more preferably 90%, and most preferably 95% or even 99% identity with all or part of a naturally occurring 90 kD kinase sequence. The length of comparison sequences will be at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring 90 kD kinase by alterations in primary sequence. These include genetic variants, both natural and induced (for example, resulting from random mutagenesis by irradiation or exposure to ethanemethylsulfate or by site-specific mutagenesis as described Ausubel et al., 1994. Also included are cyclized peptides molecules and analogs which contain residues other than L-amino acids, e.g., D-amino acids or non-naturally occurring or synthetic amino acids, e.g., β or γ amino acids.

In addition to full-length polypeptides, the invention also includes 90 kD kinase fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of 90 kD kinases can be generated by methods known to those skilled in the art or may result from normal protein processing (e.g., removal of amino acids from the nascent polypeptide that are not required for biological activity or removal of amino acids by alternative mRNA splicing or alternative protein processing events).

In another aspect the invention features a 90 kD kinase assay for cancers other than leukemias. Levels of active (autophosphorylated) 90 kD kinase (or RING3) may be elevated in a wide range of cancers, including: melanomas, hepatocarcinomas, astrocytomas, lymphomas, and epithelial cancers. For these and other cancers, diagnostic assays similar to those outlined above for the detection of leukemic cells will be useful.

All publications and patent applications mentioned in this specification are herein incorporated by reference to the same extent as if each independent publication or patent application was specifically and individually indicated to be incorporated by reference.

REFERENCES

Adams et al., Nature 349:694–697, (1991).
Ahn et al., J. Biol. Chem. 265:11487–11494, (1990)
Ahn and Krebs, J. Biol. Chem. 265:114951–11501, (1990).
Anderson et al., Nature 343:651–653, (1990).
Ausubel et al., Current Protocols in Molecular Biology, John Wiley & Sons, New York, (1994).
Baeuerle and Baltimore, Cell 53:211–217, (1988a).
Baeuerle and Baltimore, Science 242:540–546, (1988b).
Banerjee, et al., Proc. Nat'l. Acad. Sci. USA 87:8550–8554 (1990)
Beck et al., DNA Seq. 2:203–210, (1992).
Blenis, Cancer Cells 3:445–449, (1991).
Bohmann, Cancer Cells 2:337–344, (1990).
Boulton et al., Science 249:64–67, (1991).
Chen et al., Mol. Cell. Biol. 12:915–927, (1992).
Chung et al., Proc. Nat'l. Acad. Sci. USA 88:4981–4985, (1991) .
Cicirelli et al., FEBS Lett. 241:195–201, (1988)
Czech et al., J. Biol. Chem. 263:11017–11020, (1988).
Devoto et al., Cell 68:167–176, (1992).
Digan et al., Dev. Biol. 114:161–169, (1986).
Dignam et al., Nucl. Acids Res. 11:1475–1489, (1983).
Dikstein et al., Cell 69:751–757, (1992).
Djabali et al., Nature Genet. 2:113–118, (1992).
Feaver et al., Cell 67:1223–1230, (1991).
Farrell and Martin, J. Biol. Chem. 264:20723–20729, (1989).
Forquignon, Wilhelm Roux's Arch. Dev. Biol. 190:132–138, (1981).
FitzGerald et al., Internal. J. Rad. Oncology 21:1203–1210, (1991).
Gans et al., Genetics 96:887–902, (1980).
Gazdar et al., Blood 55:409–417, (1980).
Ginty et al., Science, 260:238, (1993).
Gotoh et al., Eur. J. Biochem. 193:661–669, (1990)
Griffits et al., Oncogene 7:1391–1399, (1992).
Gu et al., Cell 71:701–708, (1992).
Hammerling et al., In Monoclonal Antibodies and T Cell Hybridomas, Elsevier, N.Y., (1981).
Hanks, Curr. Biol. 1:369–383, (1991).
Hanks et al., Science 241:42–52, (1988).
Hao et al., Mol. Cell. Biol. 11:1180–1183, (1991)
Haynes et al., Dev. Biol. 134:246–257, (1989).
House and Kemp, Science 238:1726, (1987).
Hunter and Kann, Cell 70:375–387, (1992).
Ingham, Cold Spring Harbor Symp. Quant. Biol. 50:201–208, (1985).
Jackson, Trends Cell Biol. 2:104–108, (1992)
Jackson et al. Cell 63:155–165, (1990).
Kemp et al., Proc. Nat'l. Acad. Sci. USA 80:7471–7475, (1983)
Kemp and Pearson, Trends Biochem. Sci. 15:342–346, (1990).
Kemp et al., J. Biol. Chem. 252:4888–4894, (1977).
Kipreos and Wang, Science 256:382–385, (1992).
Kohler et al., Nature 256:495, (1975).
Kohler et al., Eur. J. Immunol. 6:511, (1976a).
Kohler et al., Eur. J. Immunol. 6:292, (1976b).
Kozma et al., Proc. Nat'l. Acad. Sci. USA 87:7365–7369, (1990).
Kuenzel and Krebs, Proc. Nat'l. Acad. Sci. USA 82:737–741, (1985).
Laemmli, Nature 227:680–685, (1970).
Leach et al., J. Cell Biol. 109:685–695, (1989).
Lewis et al., J. Biol. Chem. 265:947–954, (1990).
Lin and Green, Cell 64:971–981, (1991).
Lu et al., Nature 358:641–645, (1992).
Maru and Witte, Cell 67:459–468, 1991.
Mazo et al., Proc. Nat'l. Acad. Sci. USA 87:2112–2116, (1990).
Mitchell et al., Biochem. J. 261:131–136, (1989).
Moller and Amons, FEBS Lett. 186:1–7, (1985).
Nigg et al., EMBO J. 4:2801–2806, (1985).
Pearson et al., J. Biol. Chem. 260:14471–14476, (1985).
Pelech et al., Proc. Nat'l. Acad. Sci. USA 83:5968–5972, (1986).
Pelech et al., Biochem. Cell. Biol. 68:1297–1330, (1990).
Pelech et al., In: Insulin-like growth factors and their receptors in the central nervous system. Mohan et al. eds. Plenum, New York. pp. 27–46, (1987).
Pulverer et al. Nature 353:670–674, (1991).
Rubin et al., J. Biol. Chem. 253:7570–7579, (1978)
Sanghera et al., FEBS Lett. 273:223–226, (1990).
Schaap et al., Eur. J. Biochem. 191:431–435, (1990).
Tkachuk et al., Cell 71:691–700, (1992).
Van Etten et al., Cell 58:669–678, (1989).
Vik et al., Proc. Nat'l. Acad. Sci. USA 87:2685–2689, (1990)
Voncken et al., Blood 79:1029–1036, (1992).
Watson et al., Proc. Nat'l. Acad. Sci. USA 79:4078–4082, (1982).
Weiss et al., J. Immunol. 133:123–128, (1984)
Wu et al., Cell 63:687–695, (1990)
Yu et al., J. Biol. Chem. 262:16677–16685, (1987).

---

What is claimed is:

1. A method of detecting leukemic cells associated with acute lymphoblastic leukemia or chronic lymphocytic leukemia in a biological test sample, said method comprising measuring the activity of a RING3-related kinase in said biological test sample, wherein said activity is phosphorylation of a substrate of a RING3-related kinase or autophosphorylation of a RING3-related kinase, an increase in said activity relative to a control sample being indicative of the presence of leukemic cells.

2. The method of claim 1 wherein said activity is measured by assaying the autophosphorylation activity of a RING3-related kinase.

3. The method of claim 1 wherein said activity is measured by assaying the phosphorylation activity of a RING3-related kinase.

4. The method of claim 1 wherein said activity is measured by assaying phosphorylation of a substrate of a RING3-related kinase.

5. The method of claim 1 wherein said RING3-related kinase is the 90 kD kinase.

6. The method of claim 1 wherein said RING3-related kinase is RING3.

7. The method of claim 1 further comprising measuring said RING3-related kinase activity in a first biological test sample and second biological test sample.

8. The method of claim 2 wherein autophosphorylation activity is measured by immunological methods.

9. The method of claim 7 wherein said first biological test sample and said second biological test sample are obtained from the same patient at different times.

10. A kit for detecting leukemic cells in a biological sample, said kit comprising a substantially pure antibody that specifically recognizes an autophosphorylated form of a RING3-related kinase.

* * * * *